United States Patent [19]

Bussler

[11] Patent Number: 5,502,025
[45] Date of Patent: *Mar. 26, 1996

[54] SAFENING HERBICIDAL PYRAZOLYLSULFONYLUREAS

[75] Inventor: Brett H. Bussler, St. Louis Park, Minn.

[73] Assignee: Monsanto Company, St. Louis, Mo.

[ * ] Notice: The term of this patent shall not extend beyond the expiration date of Pat. No. 5,256,630.

[21] Appl. No.: 427,762

[22] Filed: Apr. 25, 1995

Related U.S. Application Data

[63] Continuation of Ser. No. 926,510, Aug. 14, 1992, abandoned, which is a continuation-in-part of Ser. No. 748,582, Aug. 22, 1991, abandoned, which is a continuation-in-part of Ser. No. 459,228, Dec. 29, 1989, Pat. No. 5,256,630, which is a continuation-in-part of Ser. No. 212,621, Jul. 1, 1988, Pat. No. 5,225,570, which is a continuation-in-part of Ser. No. 84,786, Aug. 13, 1987, abandoned.

[51] Int. Cl.$^6$ .................................................. A01N 25/32
[52] U.S. Cl. ........................................... 504/107; 504/108
[58] Field of Search ................................. 504/105, 106, 504/107, 104

[56] References Cited

U.S. PATENT DOCUMENTS

| | | | |
|---|---|---|---|
| 4,668,277 | 5/1987 | Yamamoto et al. | 504/215 |
| 4,954,164 | 9/1990 | Suzuki et al. | 504/213 |
| 5,108,482 | 4/1992 | Lang et al. | 71/76 |
| 5,201,933 | 4/1993 | Miller | 504/108 |
| 5,256,630 | 10/1993 | Bussler | 504/134 |

FOREIGN PATENT DOCUMENTS

| | | |
|---|---|---|
| 0284036 | 12/1986 | European Pat. Off. . |
| 304409 | 2/1989 | European Pat. Off. . |
| 0365484 | 10/1989 | European Pat. Off. . |
| 0397602 | 11/1990 | European Pat. Off. . |

OTHER PUBLICATIONS

The Agrochemicals Handbook, Royal Society of Chemistry, Nottingham, England, Aug. 1987, p. A004.

*Primary Examiner*—Allen J. Robinson
*Assistant Examiner*—Brian Bembenick
*Attorney, Agent, or Firm*—William I. Andress; Grace L. Bonner; Richard H. Shear

[57] ABSTRACT

The disclosure herein relates to the safening of crops from injury by herbicidal pyrazolosulfonylureas alone or combined with co-herbicides from various classes of chemistry, using various antidotal compounds known in the art.

8 Claims, No Drawings

SAFENING HERBICIDAL PYRAZOLYLSULFONYLUREAS

This is a continuation of application Ser. No. 07/926,510, filed Aug. 14, 1992, which is a continuation-in-part of application Ser. No. 07/748,582, filed Aug. 22, 1991, now abandoned, which is a continuation-in-part of application Ser. No. 07/459,228, filed Dec. 29, 1989, now U.S. Pat. No. 5,256,630, which is a continuation-in-part of application Ser. No. 07/212,621, filed Jul. 1, 1988, now U.S. Pat. No. 5,225,570, which is a continuation-in-part of application Ser. No. 07/084,786, filed Aug. 13, 1987, now abandoned.

FIELD OF THE INVENTION

The field of this invention pertains to the safening of herbicidal pyrazolylsulfonylureas alone or in the presence of various co-herbicidal compounds, especially α-chloroacetamides.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antagonists", "antidotes" or "safeners".

Weed control for crops, especially corn crops, is one of the oldest and most highly developed areas in weed science. For a herbicide product to be accepted commercially for corn crops, such herbicide product must provide a relatively high level of control of both grassy and broadleaf weeds in corn, in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide or mixture of herbicides in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

Among the various classes of compounds found to be suitable for various herbicidal purposes are the α-haloacetanilides and sulfonylureas. The former herbicides in commercial embodiments include, e.g., alachlor, acetochlor, metolachlor, etc., are excellent preemergence or early post emergence herbicides for controlling annual grasses and many broadleaved weeds in corn, peanuts, soybeans and other crops, while some of the latter herbicides, exemplified by chlorsulfuron, thifensulfuron methyl, chlorimuron ethyl, triasulfuron, metsulfuron methyl, bensulfuron methyl and the like, may be used as a foliar- or soil-applied herbicide suitable for the control of many annual and perennial broadleaved species in asparagus, cereals, corn, grain sorghum, sugarcane, soybean and other crops and woody brush and vine control in pasture, rangeland and cropland. Other sulfonylureas can be used in preplant or preemergence applications.

It is a common agronomic practice to use various antidotal compounds to reduce the phytotoxicity of some herbicides to various crops. For example, flurazole (active ingredient in SCREEN® safener) is used as a seed dressing to protect sorghum seed from alachlor (active ingredient in LASSO® herbicide). Similarly, cyometrinil (active ingredient in CONCEP® safener) has been used as a grain sorghum seed safener for use with metolachlor and oxabetrinil (active ingredient in CONCEPII® safener) is also used to safen sorghum seed from injury by metolachlor. Cyometrinil is also described in U.S. Pat. No. 4,070,389 as an antidote against chloroacetanilide and thiocarbamate herbicides in millet and rice. The compound N,N-diallyl dichloroacetamide (common name "dichlormid"; code number R-25788) is used to safen corn from injury by the thiocarbamate 5-ethyl-N,N-dipropylthiocarbamate (active ingredient in ERADICANE® herbicide) and by acetochlor (active ingredient in WENNER® herbicides). The antidotal compound "AD-67" is used to safen corn from injury by acetochlor in the commercial herbicides GUARDIAN® and ACENIT®.

It is also disclosed in the literature to use the safener fenchlorim to safen the α-chloroacetanilide herbicide pretilachlor alone or in the presence of a sulfonylurea having the common name "cinosulfuron" (active ingredient in SOFIT® SUPER herbicide). Fenchlorim and cinosulfuron are identified by chemical name infra. Cinosulfuron is characterized by substituted-phenylsulfonyl- and substituted-triazinyl radicals on the respective urea nitrogen atoms. It is also known to use a variety of safeners to safen the sulfonylurea having the common name "primisulfuron" (active ingredient in BEACON® herbicide). Primisulfuron is characterized by substituted-phenylsulfonyl- and substituted-pyrimidinyl radicals on the respective urea nitrogen atoms; its chemical structure is identified below.

It has also been disclosed in the prior art to use 1,8-naphthalic anhydride, R-25788 and cyometrinil to safen cereal crops, e.g., corn, wheat, rice and sorghum against certain sulfonylureas characterized by substituted-phenylsulfonyl- and either substituted-pyrimidinyl- or -triazinyl radicals on the respective urea nitrogen atoms (U.S. Pat. No. 4,343,649). Another reference (EP Application No. 147365, published Jul. 3, 1985) also discloses the safening of a class of sulfonylureas similar to those in said U.S. '649 patent with the same safeners and two additional ones, i.e., R-28725 and flurazole; the chemical identities of the safeners disclosed in these two references is described below.

Applicant's assignee has published patent applications relating to the use of various 5-heterocyclic-substituted oxazolidine dichloroacetamide safeners for use with a variety of herbicides including α-chloroacetanilides and sulfonylureas and mixtures thereof.

Prior to my discovery detailed herein it was not known to my knowledge to safen pyrazolylsulfonylurea herbicides, although such herbicides, per se, were known, e.g., from U.S. Pat. Nos. 4,668,277 and 4,931,081 and EP Application Publication Nos. 282,613 (Sep. 21, 1988), 087,780 (Aug. 18, 1982) and South African Published Application 83/03850 (Nov. 28, 1983).

It is an object of this invention to provide compositions of pyrazolylsulfonylureas in combination with antidotes therefor, optionally containing a coherbicide, which compositions are useful to reduce injury to crops, especially corn, due to phytotoxicity of said herbicides.

SUMMARY OF THE INVENTION

The present invention relates to herbicidal compositions comprising pyrazolylsulfonylurea derivatives and antidotal compounds therefor to reduce injury to various crops, particularly corn, from the phytotoxic effects of said herbicide when used alone or in combination with other compounds, particularly α-haloacetamides and α-haloacetanilides, as co-herbicides. Except where noted herein the term "α-haloacetamides" generically includes α-haloacetanilides as a subgroup (which require a phenyl or substituted phenyl attached to the acetamide nitrogen atom) and acetamides which have substituents other than a (un)substituted phenyl.

In more particular, in a major aspect, this invention relates to a composition comprising:

(a) a herbicidal compound having the formula

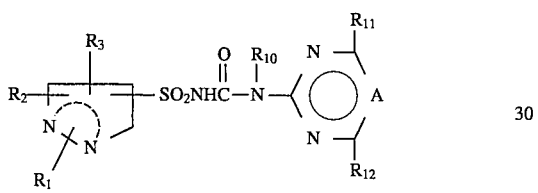

wherein
$R_1$ is H, $C_{1-3}$ alkyl or phenyl;
$R_2$ is H, $C_{1-3}$ alkyl or halogen;
$R_3$ is $R_2$, $NO_2$ or $COOR_4$;
$R_4$ is $C_{1-3}$ alkyl, $C_{2-3}$ alkenyl, $N(R_5)(R_6)$, $SO_2N(R_7)(_8)$ or $SO_2R_9$;
$R_5$–$R_9$ are $C_{1-3}$ alkyl;
$R_{10}$ is H or $C_{1-3}$ alkyl;
$R_{11}$ and $R_{12}$ are independently $C_{1-3}$ alkyl or alkoxy, halogen or $N(R_{13})(R_{14})$;
$R_{13}$ and $R_{14}$ are $C_{1-3}$ alkyl and
A is CH or N and (b) an antidotally-effective amount of
(i) a compound of the formula

wherein
$R_{15}$ can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynyloxy; haloalkoxy; thiocyanatoalkyl; alkenylaminoalkyl; alkylcarboalkyl; cyanoalkyl; cyanatoalkyl; alkenylaminosulfonalkyl; alkylthioalkyl; haloalkylcarbonyloxyalkyl, alkoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

$R_{16}$ and $R_{17}$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substitutents can be selected from alkyl, halogen, haloalkyl, alkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylene-thienyl; α-haloalkylacetamidophenylalkyl; α-haloalkylacetamidonitrophenylalkyl; α-haloalkylacetamidohalophenylalkyl; cyanoalkenyl;

$R_{16}$ and $R_{17}$ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl; benzoalkylpyrrolidinyl; oxazolidinyl; perhydrooxazolidinyl; alkyloxazolidyl; furyloxazolidinyl; thienyloxazolidinyl; pyridyloxazolidinyl; pyrimidinyloxazolidinyl; benzooxazolidinyl; $C_{3-7}$ spirocycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl; isoquinolinyl; dihydro-, tetrahydro- and perhydroquinolyl- or -isoquinolyl; indolyl and di- and perhydroindolyl and said combined $R_1$ and $R_2$ members substituted with those independent $R_1$ and $R_2$ radicals enumerated above; or
(ii) one of the following compounds
α-[(Cyanomethoxy)imino]benzeneacetonitrile (common name "cyometrinil"),
α-[(1,3-Dioxolan-2-yl-methoxy)imino]benzeneacetonitrile (common name "oxabetrinil"),
O-[1,3-Dioxolan-2-ylmethyl]-2,2,2-trifluoromethyl-4'-chloroacetophenone oxime (code number "CGA-133205"),
Benzenemethamine, N-[4-(dichloromethylene)-1,3-diothiolan-2-ylidene]-α-methyl, hydrochloride, 1,8-Naphthalic anhydride, 4,6-Dichloro-2-phenylpyrimidine (common name "fenchlorim"),
2-Chloro-N-[1-(2,4,6-trimethylphenyl)ethenyl]acetamide,
Ethylene glycol acetal of 1,1-dichloroacetone,
1,3-Dioxolane, 2-(dichloromethyl)-2-methyl-,
5-Thiazolecarboxylic acid, 2-chloro-4-(trifluoromethyl)-, (phenylmethyl)ester (common name "flurazole"),
Phosphorothioic acid, O,O-diethyl (-(3-methylphenyl)ester,
4-Pentenenitrile, 2-methyl-2-[(4-methylphenyl)thio]-,
5-Chloro-8-(cyanomethoxy)quinoline,
1-Methylhexyl-2-(5-chloro-8-quinolinoxy)acetate,
O-(Methoxycarbonyl)-2-(8-quinolinoxy)acetamide oxime,
5-Oxazolecarboxylic acid, 2-[(2,2-dimethylethyl)amino]-4-(trifluoromethyl)-, ethyl ester,
Acetic acid, (diphenylmethoxy)-, methyl ester (Code No. MON-7400),
Allyl-N-methyldithiocarbanilate, 4-Isoxazolecarboxylic acid, 5-(2,4-dichlorophenyl)-, ethyl ester,
Pyrimidine, 4,6-dichloro-2-phenyl-,
4-Pentenenitrile, 2-methyl-2-[(4-methylphenyl)thio]-,
Acetonitrile, [(5-chloro-8-quinolinyl)oxy]-,
Acetamide 2-(diphenylmethoxy)-N-methyl-,
Glycine, N-[bis(4-methoxyphenyl)methyl]-, ethyl ester,
Glycine, N-[bis(4-chlorophenyl)methyl]-, ethyl ester,
Acetic acid, [(10,11-dihydro-5H-dibenzo[1,d]cyclohepten-5-yl)oxy]-, 1,1-dimethylethyl ester,
Ethanethioamide, 2-(diphenylmethoxy)-,
Acetic acid, (diphenylmethoxy)-, propyl ester,
Acetic acid, (diphenylmethoxy)-, 2,2,2-trifluoroethyl ester,
Acetic acid, {phenyl[3-(trifluoromethyl)phenyl]methoxy}-, 2-methyl-2-propanamine salt,
Acetic acid, (diphenylmethoxy)-, phenyl ester,
Ethanethioic acid, 2-(diphenylmethoxy)-, S-ethyl ester,
Acetic acid, (diphenylmethoxy)-, 2-cyanoethyl ester,
Acetic acid, {phenyl[3-(trifluoromethyl)phenyl]methoxy}-, 2,2,2-trifluoroethyl ester,
Acetic acid, (diphenylmethoxy)-, 2-propynyl ester,
Acetic acid, (diphenylmethoxy)-, 3-furanylmethyl ester,
Acetic acid, [bis(2,6-dimethylphenyl)methoxy]-,
Acetic acid, (diphenylmethoxy)-, 3-nitrophenyl ester,
Acetic acid, {[bis(2,6-dimethylphenyl)]methoxy}-, ethyl ester,
Acetic acid, (diphenylmethoxy)-, 1-cyano-1-methylethyl ester,
5-Thiazolecarboxylic acid, 2-chloro-4-(trifluoromethyl)-, ethyl ester,
5-Thiazolecarboxylic acid, butyl ester, 2-chloro-, 4-(trifluoromethyl)-,
5-Thiazolecarboxylic acid, 2-chloro-, hexyl ester, 4-(trifluoromethyl)-,
5-Thiazolecarboxylic acid, 2-chloro-4-(trifluoromethyl)-, octyl ester,
5-Thiazolecarboxylic acid, 2-chloro-4-(trifluoromethyl)-, phenyl ester,
5-thiazolecarboxylic acid, 2-chloro-4-(trifluoromethyl)-,
5-Thiazolecarboxylic acid, 2-[bromo-4-(trifluoromethyl)]-, ethyl ester,
5-Thiazolecarboxylic acid, 2-iodo-4-(trifluoromethyl)-, ethyl ester,
5-Thiazolecarboxylic acid, 2-chloro-4-(trifluoromethyl)-, 1-methylethanamine salt,
Benzylamine-, (alpha-methyl-, N-4-(methyl)-1,3-dithiol-2-ylidene) hydrochloride,
Pyridine, N-oxide, 2-(3,4,5,6-tetrachloro-2-pyridylthio)-,
Acetic acid, [3,5-bis(trifluoromethyl)phenoxy]-,
Propanamide, 2-chloro-N-[5-iodo-4-(trifluoromethyl)-2-thiazolyl]-,
Cyclopropanecarbonitrile, 1-[(3,4-dimethylphenyl)thio]-,
Propanenitrile, 3-[[2-(1,1-dimethylethyl)phenyl]thio]-,
4-Pentenenitrile, 2-methyl-2-[[4-(1-methylethyl)phenyl]thio]-,
Ethanimidamide, N'-[(methoxycarbonyl)oxo]-2-(8-quinolinyloxy)-,
1(3H)-Isobenzofuranone, 3-[2-(2,5-dimethoxyphenyl)-2-oxoethyl]-,
Acetic acid, 2-(diphenylmethoxy)-sodium salt, hemihydrate,
Acetic acid, 2-(diphenylmethoxy)- or
Acetic acid, (diphenylmethoxy)-, 2-propanamine salt.

Preferred pyrazolylsulfonylurea compounds for use herein are those according to Formula IA below, a subgroup of Formula I compounds:

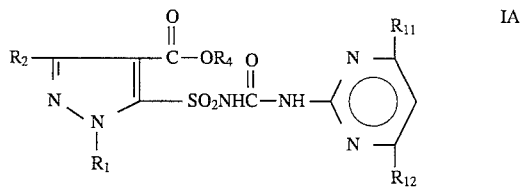

wherein $R_1$ and $R_4$ are $C_{1-3}$ alkyl;

$R_2$ is H, $C_{1-3}$ alkyl, bromo or chloro;
and $R_{11}$ and $R_{12}$ are independently $C_{1-3}$ alkyl or alkoxy.

Still more preferred species according to Formula IA are those wherein $R_1$ and $R_4$ are methyl or ethyl;

$R_2$ is H, methyl, bromo or chloro and $R_{11}$ and $R_{12}$ are independently methyl or methoxy.

Among the pyrazolylsulfonylurea species of particular interest herein are mentioned the following species:

N-[(4-methoxy-6-methylpyrimidin-2-yl)aminocarbonyl]-3-chloro-4-methoxy-carbonyl-1-methylpyrazole-5-sulfonamide;

N-[(4,6-dimethoxypyrimidin-2-yl)aminocarbonyl]-3-chloro-4-methoxycarbonyl-1-methylpyrazole-5-sulfonamide;

N-[(4-methoxy-6-methylpyrimidin-2-yl)aminocarbonyl]-3-chloro-4-ethoxycarbonyl-1-methylpyrazole-5-sulfonamide;

N-[(4,6-dimethoxypyrimidin-2-yl)aminocarbonyl]-3-chloro-4-ethoxycarbonyl-1-methylpyrazole-5-sulfonamide;

N-[(4-methoxy-6-methylpyrimidin-2-yl)aminocarbonyl]-3-bromo-4-ethoxycarbonyl-1-methylpyrazole-5-sulfonamide;

N-[(4,6-dimethoxypyrimidin-2-yl)aminocarbonyl]-3-bromo-4-ethoxy-carbonyl-1-methylpyrazole-5-sulfonamide and N-[(4,6-dimethoxy-pyrimidin-2-yl)-aminocarbonyl]-4-ethoxycarbonyl-1-methylpyrazole-5-sulfonamide.

The most preferred species of pyrazolylsulfonylurea compounds according to this invention are:

N-[(4,6-dimethoxypyrimidin-2-yl)aminocarbonyl]-3-chloro-4-methoxycarbonyl-1-methylpyrazole-5-sulfonamide (code number NC-319) and N-[4,6-dimethoxypyrimidin-2-yl)aminocarbonyl]-4-ethoxycarbonyl-1-methylpyrazole-5-sulfonamide (code number NC-311).

One group of preferred antidotal compounds includes those according to Formula II wherein $R_{15}$ is $C_{1-3}$ haloalkyl, $R_{16}$ and $R_{17}$ are independently $C_{2-4}$ alkenyl or haloalkenyl or 2,3-dioxolan-2-yl-methyl and $R_{16}$ and $R_{17}$ when combined form a $C_{4-10}$ saturated or unsaturated heterocyclic ring containing O, S and/or N atoms and which may be substituted with $C_{1-5}$ alkyl, haloalkyl, alkoxy, or alkoxyalkyl or haloacyl groups. The preferred haloalkyl $R_{15}$ member in Formula II is dichloromethyl. Preferred species in this group of antidotal compounds are N,N-diallyl-dichloroacetamide and N-(2-propenyl)-N-(1,3-dioxolanylmethyl)dichloroacetamide.

Still more preferred antidotal compounds according to Formula II is a group of substituted 1,3-oxazolidinyl dichloroacetamides having the formula

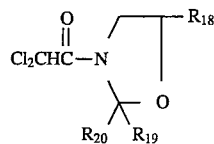

III wherein $R_{18}$ is hydogen, $C_{1-4}$ alkyl, alkylol, haloalkyl or alkoxy, $C_{2-6}$ alkoxyalkyl, a bicyclic hydrocarbon radical having up to 10 carbon atoms, phenyl or a saturated or unsaturated heterocyclic or heterocyclic methyl radical having $C_{4-10}$ ring atoms and containing O, S and/or N atoms, or said phenyl and heterocyclic(methyl) radicals substituted with one or more $C_{1-4}$ alkyl, haloalkyl, alkoxy, alkoxyalkyl, halogen or nitro radicals, and $R_{19}$ and $R_{20}$ are independently hydrogen, $C_{1-4}$ alkyl or haloalkyl, phenyl or a heterocyclic(methyl) $R_{18}$ member or together with the carbon atom to which they are attached may form a $C_3$–$C_7$ spiro-cycloalkyl group.

Preferred members according to Formula III are those wherein $R_{18}$ is one of said heterocyclic members and $R_{19}$ and $R_{20}$ are independently methyl, trifluoromethyl or when combined with the carbon atom to which attached form a $C_5$ or $C_6$ cycloalkyl radical.

Preferred antidotal compounds according to Formula III are the following compounds:

Oxazolidine, 3-(dichloroacetyl)-2,2,5-trimethyl-, (code number R-29148),

Oxazolidine, 3-(dichloroacetyl)-2,2-dimethyl-, code number R-28725 and AD-2),

Oxazolidine, 3-(dichloroacetyl)-2,2-dimethyl-5-phenyl-,

Oxazolidine, 3-(dichloroacetyl)-2,2-dimethyl-5-(2-furanyl)-,

Oxazolidine, 3-(dichloroacetyl)-2,2-dimethyl-5-(2-thienyl)-,

Pyridine, 3-[3-(dichloroacetyl)-2,2-dimethyl-5-oxazolidinyl]-, 4-(dichloroacetyl)-1-oxa-4-azaspiro-(4,5)-decane (code number "AD-67").

Another group of dichloroacetamide antidotal compounds according to Formula II are the following compounds:

4-(Dichloroacetyl)-3,4-dihydro-3-methyl-2H-2,4-benzoxazine (common name "benoxychlor"; Code No. "CGA-154281"), Ethanone, 2,2-dichloro-1-(1,2,3,4-tetrahydro-1-methyl-2-isoquinolinyl)-, N-(Dichloroacetyl)-1,2,3,4-tetrahydroquinaldine, 1-(Dichloroacetyl)1,2,3,4-tetrahydroquinoline, Cis/trans-piperazine, 1,4-bis(dichloro 1,4-acetyl)-2,5-dimethyl-, N,N-dipropenyl dichloroacetamide, N-(2-propenyl)-N-(1,3-dioxolan-2-ylmethyl) dichloroacetamide (code number PPG-1292), 1,5-Diazacyclononane, 1,5-bis-(dichloroacetyl, 1-Azaspiro[4,4]nonane, 1-(dichloroacetyl), Pyrrolo[1,2-a]-pyrimidine-[6(2H)]-one, 1-(dichloroacetyl)hexahydro-3,3,8a-trimethyl, 2,2-Dimethyl-3-(dichloroacetyl)-1,3-oxazole and 2,2-Dimethyl-5-methoxy-3-(dichloroacetyl)-1,3-oxazole.

Still another preferred group of antidotal compounds are those enumerated in Paragraph (b) (ii) in the above Summary of the Invention.

Particular utility for the compositions according to this invention is to be found, e.g., in the crops corn, rice, wheat, cereals (e.g., barley, rye), soybeans, sugarbeet, cotton, etc.

Another aspect of this invention is the combination of various co-herbicides in mixtures containing the pyrazolylsulfonylurea herbicide(s) and safener(s), to broaden the spectrum of control of undesirable plants associated with valuable crop plants.

Herbicidal compounds which may be used as co-herbicides with the pyrazolylsulfonylurea compounds of Formula I come from a wide variety of known chemical classes, e.g., α-chloroacetamides, thiocarbamates, imidazolinones, pyridines, triazines, heterophenyl ethers, diphenyl ethers, ureas, sulfonylureas, azolopyrimidine sulfonamides, thiazoles, pyrazoles, isoxazoles, nitroanilines, pyrrolidinones, aromatic and heterocyclic di- and triketones, etc. Individual members of the foregoing classes may be derivatives having one or more substituents selected from a wide variety of radicals commonly and suitably used in herbicidal molecules.

A most preferred class of compounds useful as the co-herbicidal component herein includes α-chloroacetamides according to Formula IV

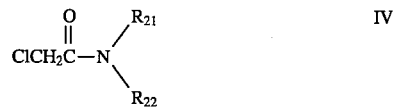

IV wherein $R_{21}$ and $R_{22}$ are independently hydrogen; $C_{1-8}$ alkyl, alkoxy, alkoxyalkyl, acylaminomethyl, acyl-lower alkyl-substituted aminomethyl; cycloalkyl, cycloalkylmethyl, mono- or polyunsaturated alkenyl, alkynyl, cycloalkenyl, cycloalkenylmethyl having up to 8 carbon atoms; phenyl; or $C_{4-10}$ heterocyclyl or heterocyclylmethyl containing from 1 to 4 ring hetero atoms selected independently from N, S or O; and wherein said $R_{21}$ and $R_{22}$ members may be substituted with alkyl, alkenyl, alkynyl, alkenyloxy, alkynyloxy, alkoxy, alkoxyalkyl, alkoxycarbomethyl or ethyl having up to 8 carbon atoms; nitro; halogen; cyano; amino or $C_{1-4}$ alkyl-substituted amino; and wherein $R_{21}$ and $R_{22}$ may be combined together with the N atom to form one of said heterocyclyl or substituted-heterocyclyl members.

Preferred herbicidal compounds according to Formula IV are those wherein the $R_{21}$ member is an alkoxyalkyl radical of the structure —B—O—$R_{23}$, wherein B and $R_{23}$ are linear or branched-chain alkyl radicals having a combined total of up to 8 carbon atoms; or a substituted or unsubstituted $C_{4-10}$ heterocyclyl or heterocyclylmethyl radical containing from 1 to 4 ring hetero atoms selected independently from N, S or O atoms and the $R_{22}$ member is also one of said heterocyclyl or heterocyclylmethyl radicals or an optionally-substituted phenyl radical. Preferably the phenyl radical is substituted with alkyl groups, especially in the ortho positions. Similarly, some preferred heterocyclic members are substituted with alkyl or alkoxy radicals.

Among the more important heterocyclic $R_{21}$ and/or $R_{22}$ members of Formula IV are mentioned independently, the furanyl, thienyl, pyrazolyl, pyrrolyl, isoxazolyl, isothiazolyl, triazolyl, imidazolyl, and pyrimidinyl radicals and their analogs having a methylene (—CH$_2$—) moiety connecting the heterocyclic radical to the acetamide nitrogen atom, e.g., pyrazol-1-ylmethyl. When the heterocyclic radical is attached directly to the amide nitrogen (with no intervening methylene moiety), the attachment may be through a ring carbon atom or a ring hetero atom as appropriate. Other important $R_{21}$ and/or $R_{22}$ members include the following: propynyl, alkoxycarbomethyl or -ethyl, alkoxyiminoalkyl, benzyl, hydroxyalkyl, haloalkoxy and -alkoxyalkyl, cyanoalkoxy and -alkoxyalkyl, methyl, ethyl, propyl, butyl and their isomers, and the like.

Among preferred species of Formula IV are mentioned N-(2,4-dimethylthien-3-yl)-N-(1-methoxyprop-2-yl)-2-chloroacetamide; N-(1H-pyrazol-1-ylmethyl)-N-(2,4-dimethylthien-3-yl)-2-chloroacetamide; N-(1-pyrazol-1-ylmethyl)-N-(4,6-dimethoxypyrimidin-5-yl)-2-chloroacetamide and 2-Chloro-N-isopropyl-1-(3,5,5-trimethylcyclohexen-1-yl) acetamide.

Another important subgenus of preferred α-haloacetamide compounds useful as the co-herbicidal component herein are the α-chloroacetanilides according to Formula V

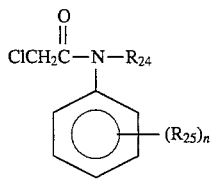

wherein
$R_{24}$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;

$R_{25}$ is hydrogen, halogen, nitro, amino, $C_{1-6}$ alkyl, alkoxy or alkoxyalkyl, and n is 0–5.

Examples of important acetamide herbicides according to Formulae IV and V are the following:

2-chloro-N-isopropylacetanilide (common name "propachlor");

2-chloro-2', 6'-diethyl-N-(methoxymethyl)acetanilide (common name "alachlor");

2-chloro-2',6'-diethyl-N-(butoxymethyl)acetanilide (common name "butachlor");

2-chloro-N-(ethoxymethyl)-6'-ethyl-o-acetotoluidide (common name "acetochlor");

Ethyl ester of N-chloroacetyl-N-(2,6-diethylphenyl)glycine (common name "diethatyl ethyl");

2-chloro-N-(2,6-dimethylphenyl)-N-(2-methoxyethyl)acetamide (common name "dimethachlor");

2-chloro-N-(2-n-propoxyethyl)-2', 6'-diethylacetanilide (common name "pretilachlor");

2-chloro-N-(2-methoxy-1-methylethyl)-6'ethyl-o-acetotoluidide (common name "metolachlor");

2-chloro-2', 6'-dimethyl-N-(1-pyrazol-1-yl-methyl)acetanilide (common name "metazachlor");

2-chloro-N-(2,6-dimethyl-1-cyclohexen-1-yl)-N-(1H-pyrazol-1ylmethyl)acetamide;

2-chloro-N-isopropyl-1-(3,5,5-trimethylcyclohexen-1-yl) acetamide (common name "trimexachlor");

2-Chloro-2'-methyl-6'-methoxy-N-(isopropoxymethyl)acetanilide;

2-Chloro-2'-methyl-6'-trifluoromethyl-N-(ethoxymethyl)acetanilide;

N-(2,4-dimethylthien-3-yl)-N-(1-methoxyprop-2-yl)-2-chloroacetamide;

N-(1H-pyrazol-2-ylmethyl)-N-(2,4-dimethylthien-3-yl)-2-chloroacetamide and

N-(1-pyrazol-1-ylmethyl)-N-(4,6-dimethoxypyrimidin-5-yl)-2-chloroacetamide.

The most preferred species of compounds according to Formula V are 2-chloro-2'-ethyl-6'-methyl-N-(ethoxymethyl)acetanilide (common name "acetochlor"), 2-chloro-2', 6'-diethyl-N-(methoxymethyl)acetanilide (common name "alachlor"), 2-chloro-2',6'-diethyl-N-(butoxymethyl)acetanilide (common name "butachlor"), 2-chloro-2'-ethyl-6'-methyl-N-(1-methyl-2-methoxyethyl)acetanilide (common name "metolachlor"), 2-chloro-2',6'-diethyl-N-(2-n-propoxyethyl)-acetanilide (common name "pretilachlor") and 2-chloro-2',6'-dimethyl-N-(pyrazolylmethyl)acetanilide (common name "metazachlor").

A larger group of preferred α-chloroacetamide and α-haloacetanilide herbicides includes the particular preferred species of Formulae IV and V identified above.

Yet another class of preferred compounds useful as the co-herbicidal component in the composition/method according to this invention are the thiocarbamates.

Examples of important thiocarbamate herbicides are the following:

cis-/trans-2,3-dichloroallyl-diisopropylthiolcarbamate (common name "diallate");

2,3,3-trichloroallyl-diisopropylthiocarbamate (common name "triallate").

Ethyl dipropylthiocarbamate (common name "EPTC");

S-ethyl diisobutylthiocarbamate (common name "butylate");

S-propyl dipropylthiocarbamate (common name "vernolate");

Examples of important co-herbicidal sulfonylureas include:

Benzenesulfonamide, 2-chloro-N-[[(4-methoxy-6-methyl-1,3,5-triazin-2-yl)amino]-carbonyl] (common name "chlorsulfuron");

Benzoic acid, 2-[[[[(4-chloro-6-methoxy-2-pyrimidin-2-yl)amino]carbonyl]amino]sulfonyl]-ethyl ester (common name "chlorimuronethyl");

2-Thiophenecarboxylic acid, 3-[[[[( 4,6-dimethoxy-1,3,5-triazin- 2-yl)amino]carbonyl]-amino]sulfonyl]-, methyl ester (common name thifensulfuron methyl; code No. "DPX M6316");

Benzoic acid, 2-[[[[(4,6-dimethyl-2-pyrimidinyl)amino] carbonyl]amino]sulfonyl]-methyl ester (common name "sulfuron methyl");

Benzenesulfonamide, 2-(2-chloroethoxy)-N-[[(4-methoxy-6-methyl-1,3,5-triazin- 2-yl)amino]-carbonyl] (common name "triasulfuron");

Benzoic acid, 2-[[[[(4-methoxy-6-methyl-1,3,5-triazin-2-yl)amino]carbonyl]amino]sulfonyl]-methyl ester (common name "metsulfuron methyl");

Benzoic acid, 2-[[[[[4,6-di (difluoromethoxy)-2-pyrimidin- 2-yl]amino]carbonyl]amino]sulfonyl]methyl ester (common name "primisulfuron");

Pyridine, 3-[[[[(4,6-dimethyl-2-pyrimidin- 2-yl)amino]carbonyl]amino]sulfonyl]-N,N-dimethylcarbamoyl (common name "nicosulfuron");

Pyridine, 3-[[[[(4,6-dimethoxy-2-pyrimidin-2-yl)amino] carbonyl]amino]sulfonyl]ethylsylfonyl (code number "DPX E9636);

Benzenesulfonamide, 2-(methoxyethoxy)-N-[[(4,6-dimethoxy-1,3,5-triazin-2-yl)amino]carbonyl] (common name "cinosulfuron")

Methyl-2-[[[[[(4,6-dimethoxy-2-pyrimidin-2-yl) amino] carbonyl]amino]sulfonyl]methyl]benzoate (common name "bensulfuron methyl");

(4,6-dimethylpyrimidin-2-yl)aminocarbonyl]-1-(1-methylethyl)-1H-imidazole-2-sulfonamide;

N-[(4-methoxy-6-methylpyrimidin-2-yl)aminocarbonyl]-1-(1-methylethyl)-1H-imidazole- 2-sulfonamide;

N-[(4,6-dimethoxypyrimidin-2-yl)aminocarbonyl]-1-(1-methylethyl)-1H-imidazole-2-sulfonamide;

N-[(4,6-dimethylpyrimidin-2-yl)aminocarbonyl]-1-ethyl-1H-imidazole-2-sulfonamide;

N-[(4-methoxy-6-methylpyrimidin-2-yl)aminocarbonyl]-1-ethyl-1H-imidazole-2-sulfonamide;

N-[(4,6-dimethoxypyrimidin-2-yl)aminocarbonyl]-1-ethyl-1H-imidazole-2-sulfonamide;

N-[(4,6-dimethoxypyrimidin-2-yl)aminocarbonyl]-5-bromo-1-methyl-1H-imidazole-4-sulfonamide.

Important co-herbicidal ureas include the following compounds:

N-(4-Chlorophenoxy) phenyl-N,N-dimethylurea;

N,N-dimethyl-N'-(3-chloro-4-methylphenyl) urea;

3-(3,4-Dichlorophenyl)-1,1-dimethylurea;

1,3-Dimethyl-3-(2-benzothiazolyl) urea;

3-(p-Chlorophenyl)-1,1-dimethylurea and

1-Butyl-3-(3,4-dichlorophenyl)-1-methylurea.

Another class of preferred compounds useful as the co-herbicidal component herein are the imidazolinones.

Examples of important imidazolinone herbicides include:

3-Quinolinecarboxylic acid, 2-[4,5-dihydro-4-methyl-4-(1-methylethyl)-5-oxo- 1H-imidazol-2-yl]-;

3-Pyridinecarboxylic acid, 2-[4,5-dihydro-4-methyl-4-(1-methylethyl)-5-oxo-1H-imidazol-2-yl]-;

Benzoic Acid, 2-[4,5-dihydro-4-methyl-4-(1-methylethyl)-5-oxo-1 H-imidazol-2-yl]-4(or 5)-methyl;

3-pyridinecarboxylic acid, 5-ethyl-2-[4-methyl-4-(1-methylethyl)-5-oxo-1H-imidazol-2-yl]-;

3-pyridinecarboxylic acid, 2-[4,5-dihydro-4-methyl-4-(1-methylethyl)-5-oxo-1H-imidazol-2-yl]-5-methyl-, ammonium salt;

2-(5-Methyl-5-trifluoromethyl-1-H-imidazol-4-on-2-yl)-pyridin-3-carboxylic acid;

2-(5-Methyl-5-trifluoromethyl-1-H-imidazol-4-on-2-yl)5-(m)ethyl isonicotinic acid;

2-[5-(1-Fluoroethyl)-5-(m)ethyl-H-imidazol-4-on-2-yl] isonicotinic acid;

2-(5-(Difluoromethyl-5-(m)ethyl-1-H-imidazol-4-on-2-yl]-5-(m)ethyl-isonicotinic acid;

2-(5-(1-Fluoroethyl)-5-(m)ethyl)-imidazol-4-on-2-yl] isonicotinic (m)ethyl ester.

Examples of important pyridine co-herbicides include:

3-Pyridinecarboxylic acid, -2(difluoromethyl)-5-4,5-dihydro-2-thiazolyl-4-(2-methylpropyl)- 6(trifluoromethyl)-, methyl ester;

3-Pyridinecarboxylic acid, 2-(difluoromethyl)-4-(2-methylpropyl)-5-(1H-pyrazol-1-ylcarbonyl)-6-(trifluoromethyl)-, methyl ester;

3,5-pyridinedicarboxylic acid, 2-(difluoromethyl)-4-(2-methylpropyl)-6-trifluoromethyl, dimethyl ester;

3,5-pyridine dicarbothioic acid, 2-(difluoromethyl)-4-(2-methylpropyl)-6-(trifluoromethyl)-, S,S-dimethyl ester;

5-(Trifluoromethyl)-4-chloro-3-(3'-[1-ethoxycarbonyl]-ethoxy-4'-nitrophenoxy)- 1-methylpyrazol;

5-(Trifluoromethyl)-4-chloro-3-(3'-methoxy-4'-nitrophenoxy)-1-methylpyrazole;

5-(Trifluoromethyl)-4-chloro-3-(3'-[1-butoxycarbonyl]-ethoxy-4'-nitrophenoxy)- 4-methylpyrazol;

5-(Trifluoromethyl)-4-chloro-3-(3'-methylsulfamoylcarbonyl propoxy-4'-nitrophenoxy)-4-methylpyrazol;

5-(Trifluoromethyl)-4-chloro-3-(3'-propoxycarbonylmethyloxime-4'-nitrophenoxy)-1-methylpyrazole;

(±)-2-[4-[[5-(Trifluoromethyl)-2-pyridinyl]oxy]phenoxy] -propanoic acid (9CI);

S,S-Dimethyl-2-(difluoromethyl)-4-isobutyl-6-trifluoromethyl-3,5-pyridinedicarbothioate;

3-(Pyridinecarboxylic Acid, 2-(difluoromethyl)-5-(4,5-dihydro-2-thiazolyl)-4-(2-methylpropyl)- 6-(trifluoromethyl)-, methyl ester;

3,5-Pyridinedicarboxylic acid, 2-(difluoromethyl)-4-(2-methylpropyl)-6-(trifluoromethyl)-, dimethyl ester;

3,5-Pyridinedicarbothioic acid, 4-(cyclopropylmethyl)-2-(difluoromethyl)-6-(trifluoromethyl)-, S,S-dimethyl ester;

Sulfoximine, N-(diethoxyphosphinyl)-S-methyl-S-phenyl-.

Examples of important co-herbicidal heterocyclyl phenyl ethers include:

5-(trifluoromethyl)-4-chloro-3-(3'-[1-ethoxycarbonyl]-ethoxy-4'-nitrophenoxy)- 1-methylpyrazole;

5-(trifluoromethyl)-4-chloro-3-(3'-methoxy-4'-nitrophenoxy)-1-methylpyrazole;

5-(trifluoromethyl)-4-chloro-3-(3'-[1-butoxycarbonyl]-ethoxy-4'-nitrophenoxy)- 4-methylpyrazole;

5-(trifluoromethyl)-4-chloro-3-(3'-methylsulfamoylcarbonyl propoxy-4'-nitrophenoxy)-4-methylpyrazole;

5-(trifluoromethyl)-4-chloro-3-(3'-propoxycarbonylmethyloxime-4'-nitrophenoxy)-1-methylpyrazole;

(±)-2-[4-[[5-(trifluoromethyl)-2-pyridinyl]oxy]phenoxy] propanoic acid.

Examples of important benzoic acid derivative herbicides include:

3,6-Dichloro-2-methoxybenzoic acid (common name "dicamba"), 2,5-Dichloro-3-aminobenzoic acid (common name "amiben" and "chloramiben"), 5-(2'-Chloro-4'-trifluoromethylphenoxy)-2-nitrobenzoic acid (common name "acifluorfen"), 2,6-Dichlorobenzonitrile (common name "dichlobenil"), 3,5,6-Trichloro-2-methoxybenzoic acid (common name "Tricamba"), 2,3,6-Trichlorobenzoic acid, and 2,3,5,6-Tetrachlorobenzoic acid, and salts, esters and amides of the above acids.

Yet another class of compounds useful as co-herbicides in the compositions of this invention are the azolopyrimidine sulfonamides, exemplified by the following preferred species:

5,7-dimethyl-N-(2,6-dichlorophenyl)-1,2,4-triazolo[1,5-a]-pyrimidine-2-sulfonamide;

5-Methyl-N-(2-bromo-6-chlorophenyl)-1,2,4-triazolo[1,5-a]-pyrimidine-2-sulfonamide;

5-Methyl-N-(2,6-difluoro-3-methylphenyl)-1,2,4-triazolo-[1,5-a]pyrimidine-2-sulfonamide;

5-Methyl-N-(2,6-difluorophenyl)-1,2,4-triazolo-[1,5-a]-pyrimidine-2-sulfonamide;

5,7-Dimethoxy-N-(2,6-dichloro-3-methylphenyl)-1,2,4-triazolo-[1,5-a]pyrimidine-2-sulfonamide;

5,7-Dimethoxy-N-(2-methoxy-6-trifluoromethylphenyl)-1,2,4-triazolo-[1,5-a]-pyrimidine- 2-sulfonamide;

5,7-Dimethyl-2-(N-[2-chloro, 6-propargyloxyphenyl]-sulphamoyl)-1,2,4-triazolo[ 1,5-a]-pyrimidine;

5,7-Dimethyl-2-(N-[2-chloro-6-(2-ethoxyethoxy)phenyl]-sulphamoyl)-1,2,4-triazolo[ 1,5-a]-pyrimidine;

5,7-Dimethyl-2-(N-[2-allyloxy-6-fluorophenyl]sulphamoyl)-1,2,4-triazolo[1,5-a]-pyrimidine;

5-Methoxymethyl-N-(2-chloro-6-methylphenyl)-1,2,4-triazolo-[2,5-a]-pyrimidine-2-sulfonamide;

N-(2,6-Difluorophenyl)-4,6-dimethylimidazolo[1,2-a]-pyrimidine-2-sulfonamide;

N-(2,6-Dichlorophenyl)-4,6-dimethylimidazolo[1,2-a]-pyrimidine-2-sulfonamide;

N-(2,6-Difluorophenyl)-3-cyano-4,6-dimethylimidazolo [1,2-a]-pyrimidine-2-sulfonamide;

5,7-Dimethyl-N-(2-chloro-6-methylphenyl)-1,2,4-triazolo-[1,5-a]-[4H, 7H]-dihydropyrimidine-2-sulfonamide;

7-Methyl-N-(2-chloro-6-methylphenyl)-1,2,4-triazolo-[1,5-a]-[4H, 7H]-dihydropyrimidine-2-sulfonamide;

5,7-Dimethyl-N-(2-chloro-6-ethoxyphenyl)-1,2,4-triazolo-[1,5-a]-[4H, 7H]-dihydropyrimidine-2-sulfonamide;

5-Fluoro-7-methoxy-N-(2,6-difluorophenyl)-1,2,4-triazolo[1,5-c]-pyrimidine-2-sulfonamide;

N-(2,6-Dichlorophenyl)-6,7-dihydro-5,6-dimethyl-7-oxo[1,2,4]triazole[1,5-a][ 1,3,5]-triazine-2-sulfonamide;

N-(2,6-dichlorophenyl)-6,7-dihydro-5,6-dimethyl-7-thioxo-[1,2,4]triazolo[1,5-a]-[1,3,5]-triazine-2-sulfonamide;

6,7-Dihydro-5,6-dimethyl-N-(2-methyl-6-nitrophenyl)-7-thioxo-[1,2,4]triazolo-[ 1,5-a]-[1,3,5]-triazine-2-sulfonamide;

N,(2,6-Dichlorophenyl)-6,7-dihydro-5,6-dimethyl-3-methoxycarbonyl-7-oxopyrazolo-[1,5-a]-[1,3,5]-triazine-2-sulfonamide;

N-(2,6-Difluorophenyl)-6,7-dihydro-5,6-dimethyl-3-methoxycarbonyl-7-thioxopyrazolo[1,5-a]-[ 1,3,5]-triazine-2-sulfonamide;

N-(2-Chloro-6-fluorophenyl)-6,7-dihydro-5,6-dimethyl-3-methoxycarbonyl-7-oxopyrazolo-[1,5-a][1,3,5]-triazine-2-sulfonamide;

N-(2-Chloro-6-fluorophenyl)-6,7-dihydro-5,6-dimethyl-3-methoxycarbonyl-7-thioxopyrazolo-[1,5-a][1,3,5]-triazine-2-sulfonamide;

N-(2,6-Difluorophenyl)-thiazole[3,2-b][1,2,4]triazole-2-sulfonamide;

N-5-methyl-4,5,6,7-tetrahydro-1,2,4-triazolo[1,5-a]-pyrimidine-2-yl-2-( 2,6-difluorophenyl)-sulfonamide;

N-(5,7-Dimethyl-1,2,4-triazolo[1,5-a]-pyrimidin-2-yl)-2-thiophene sulfonamide;

N-Acetyl-2,6-dichloro-N-(5,7-dimethyl-1,2,4-triazolo[1, 5-a]-pyrimidin-2-6l)-benzenesulfonamide;

N-(5,7-Dimethyl-1,2,4-triazolo[1,5-a]-pyrimidin-2-yl)-2-nitrobenzenesulfonamide;

N-(5-Amino-1,2,4-triazol-3-yl)-2,5-dichlorobenzenesulfonamide;

2-Chloro-N-(5-methyl-7-trifluoromethyl-1,2,4-triazolo [1,5-a]pyrimidin-2-yl)-benzenesulfonamide;

2-Chloro-N-(6-chloro-1,2,4-triazolo[1,5-a]-pyrimidin-2-yl)benzenesulfonamide;

N-(5,7-Dimethyl)-6,7-dihydro-[1,2,4]-triazole-[1,5-a][1, 3,5]-triazine-2-( 2,6-difluorophenyl)-sulfonamide;

N-(7-Methoxy-6,7-dihydro-[1,2,4]-triazole[2,5-a]-[1,3,5] -triazine-2-( 2,6-dichlorophenyl)sulfonamide;

N-(5-Chloro)-6,7-dihydro-[1,2,4]-triazole[1,5-a]-[1,3,5]-triazine-2-(2-acetyl-6-methylphenyl)sulfonamide;

N-(5-methoxymethyl)-6,7-dihydro[1,2,4]-triazole-[1,5-a] -[1,3,5]-triazine-2-( 2,6-difluorophenyl)-sulfonamide.

Examples of other important compounds useful as co-herbicides include:

2-Chloro-4-(ethylamino)-6-(isopropylamino)-s-triazine;

4-Amino-6-tertbutyl-3-(methylthio)as-triazine-5(4H)one;

Trifluoro-2,6-dinitro-N,N-dipropyl-p-toluidine;

Benzeneamine, N-(1-ethylpropyl)-3,4-dimethyl-2,6-dinitro-;

2-Pyrrolidinone, 3-chloro-4-(chloromethyl)-1-[3-(trifluoromethyl)phenyl], trans-;

3-Isoxazolidinone, 2-[(2-chlorophenyl)methyl]-4,4-dimethyl-;

2-Imidazolidinone, 3-[5-(1,1-dimethylethyl)-3-isoxazolyl]-4-hydroxy-1-methyl-;

2-Chloro-4-(1-cyano-1-methylethylamino)-6-ethylamino-1,3,5-triazine;

Methyl 5-(2,4-dichlorophenoxy)-2-nitrobenzoate;

1'-(Carboethoxy)ethyl-5-[2-chloro-4-(trifluoromethyl)phenoxy]-2-nitrobenzoate;

Ammonium-DL-homoalanin-4-yl(methyl)phosphinate;

1-[(2-Fluoro-4-chloro-5-(2,3-dimethylbutoxyphenyl0}tetrahydrophthalimide 2-(3,4-Dichlorophenyl)-4-methyl-1,2,4-oxadiazolidine-3,5-dione;

2,6-Dichlorobenzonitrile;

Monosodium acid methanearsonate;

Disodium methanearsonate;

2-(2-chlorophenyl)methyl-4,4-dimethyl-3-isoxazolidinone;

7-Oxabicyclo (2.2.1) heptane, 1-methyl-4-(1-methylethyl)-2-(2-methylphenylmethoxy)-, exo-;

Glyphosate and salts thereof;

(2,4-Dichlorophenoxy)acetic acid (common name "2,4-D"), and salts and esters thereof and 2-(4-Chloro-2-methylphenoxy) propionic acid (common name "mecoprop"), salts and esters thereof.

In various embodiments within the purview of this invention, the co-herbicidal component(s) in admixture with the pyrazolylsulfonylurea compounds of Formula I and a safener may comprise mixtures of various herbicides. For example, the commercial composition TRIMEC® is a mixture of dimethylamine salts of 2,4-D, mecoprop and dicamba. Many other such mixtures of 2,4-D and other herbicidal compounds are commercially available under a variety of tradenames; many of these mixtures are listed in The Pesticide Manual 9th Ed. (1991) on page 220.

The herbicides of particular and preferred interest as co-herbicides with the pyrazolyl-sulfonyl-urea compositions containing antidotes according to this invention include each of the above-mentioned species from different chemical classes of compounds exemplified as important herbicides, particularly those of current commercial interest and use and those which may be determined of commercial utility.

Co-herbicidal compounds of preference include the following:

alachlor, acetochlor, butachlor, metolachlor, pretilachlor, metazachlor, dimethachlor,

EPTC, butylate and vernolate.

The above, and other, co-herbicides may be pre-mixed with safeners of choice prior to mixing with or in any mode of combining with the pyrazolylsulfonylurea herbicides of Formula I. For example, the above listed compounds may be tank mixed or package mixed with the safeners AD-67, R-25788, R-29148, PPG-1292 or oxazolidine, 3-(dichloroacetyl)-2,2-dimethyl-5-(2-furanyl)- or other suitable safener disclosed herein and optionally other additaments, such as extenders, e.g., dietholate, etc., then applied simultaneously with or sequentially to the plant locus together with the compounds of Formula I.

The particular herbicidal compositions of preference herein are those containing the pyrazolylsulfonylureas of Formula IA and the safeners of Formula III, Formula II(b) (ii) and selected safeners from Formula II(b) (i).

The herbicidal and antidotal compounds of Formulae I–V are known in the art.

Compositions of particular and preferred interest herein include combinations of the Formula I herbicidal components NC-311 or NC-319, and the antidotal components: R-29148, PPG-1292,1AD-67 and oxazolidine, 3-(dichloroacetyl)-2,2-dimethyl-5-(2-furanyl)- and other compounds according to Formula III, said compositions optionally containing as a co-herbicidal component an α-chloroacetamide of Formulae IV or V, especially acetochlor, alachlor, butachlor, metolachlor, pretilachlor or trimexachlor.

Of further particular interest are compositions comprised of NC-311 or NC-319 as the herbicidal component; and R-25788, AD-67 or oxazolidine, 3-dichloroacetyl)-2,2-dimethyl-5-(2-furanyl)- as the antidotal component and acetochlor as the optional co-herbicidal component.

The components of the composition may comprise individual members of each class, i.e., herbicidal, co-herbicidal and antidotal components, or combinations of members of each class, particularly the herbicidal and antidotal classes. Illustrative other herbicidal compounds which may be particularly suitable as co-herbicides with the preferred Formula I class of herbicides include the species of thiocarbamates, pyridines, heterophenyl ethers, sulfonylureas, imidazolinones and azolopyrimidine sulfonamides exemplified above.

As disclosed in more detail below, the above compositions may be formed in a variety of ways, including tank mixing the said separate components for either bulk dispersal or for pre-packaging for storage, transportation, sale and use. Said compositions are also formed when the individual components are separately applied to the locus of use and there combine in contact with each other simultaneously or sequentially in any order. For example, the antidotal and/or Formula I herbicide components may be first applied to the soil separately or together, followed by application of the co-herbicidal component or the antidotal component may be applied to the seeds of the crop plant prior to planting in soil previously or subsequently treated with the Formula I and/or co-herbicidal component(s). The only caveat in forming said composition is that the antidotal component must always be present, i.e., in contact with, the herbicidal component(s) at the locus of the plant seed or plant at the time of contacting the two components together.

As used herein the term "haloalkyl" embraces radicals wherein any one or more of the carbon atoms, preferably from 1 to 4 in number, is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Where in Formulae II, V and III the halogen attached to the acetyl radical is the chlorine ion, it is contemplated that the other halogens, i.e., bromo, iodo or fluoro may be substituted for the chloro.

Preferred haloalkyl $R_{15}$ members of antidotes of Formula II are dihalomethyl, particularly dichloromethyl, while the preferred haloalkyl $R_{19}$ or $R_{20}$ member of antidotes Formula III is a tri-halogenated methyl radical, preferably trifluoromethyl.

Where the term "alkyl" is used either alone or in compound form (as in "haloalkyl"), it is intended to embrace linear or branched radicals having up to four carbon atoms, the preferred members being methyl and ethyl.

By "agriculturally-acceptable salts" of the compounds defined by any of the above formula is meant a salt or salts which readily ionize in aqueous media to form a cation or anion of said compounds and the corresponding salt anion or cation, which salts have no deleterious effect on the antidotal properties of said compounds or of the herbicidal properties of a given herbicide and which permit formulation of the herbicide-antidote composition without undue problems of mixing, suspension, stability, applicator equipment use, packaging, etc.

By "antidotally-effective" is meant the amount of antidote required to reduce the phytotoxicity level or effect of a herbicide, preferably by at least 10% or 15%, but naturally the greater the reduction in herbicidal injury the better.

By "herbicidally-effective" is meant the amount of the herbicide component (individual or plural) required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

As further detailed infra, while not necessary, the composition comprising the herbicide/antidote combination may also contain other additaments, e.g., various biocides, e.g., insecticides, fungicides, nematicides, etc., fertilizers, inert formulation aids, e.g., surfactants, emulsifiers, defoamers, dyes, extenders, etc.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous, but more complex manner, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides and herbicide combinations in various crops than in others. Thus, while a given antidotal compound may have no crop protective ability against a given herbicide in a given crop, that same antidotal compound may have a very high crop protective ability against the same given herbicide in a different crop or against a different herbicide in the same crop at the same or different rate of application or in a different application mode, i.e., PPI, PRE, seed dressing, etc.. This is an expected phenomenon.

DETAILED DESCRIPTION OF THE INVENTION

Antidote Compounds

As mentioned earlier, the antidotal compounds used in the practice of this invention are known compounds. The preferred compounds used herein are the 1,3-oxazolidine dichloroacetamides according to Formula III wherein the $R_{18}$ member is a heterocyclic radical.

Biological Evaluation

Effective weed control coupled with low crop injury is a result of treatment of a plant locus with a combination of herbicide and antidote compounds. By application to the "plant locus" is meant application to the plant growing medium, such as soil, as well as to the seeds, emerging seedlings, roots, stems, leaves, or other plant parts.

The phrase "combination of herbicide and/or antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination" (composition). Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide/antidote combinations, it is inherent that each form of application requires that in some manner, the herbicide and antidote will physically combine to form a "composition" of those agents.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide/antidote mixture may be applied to the soil, and then the seed thereafter "drilled" into the soil below the soil layer containing the herbicide/antidote mixture. The herbicide will reduce or eliminate the presence of undesirable weed plants. Where the herbicide would by itself injure the crop seedlings, the presence of the antidote will reduce or eliminate the injury to the crop seed caused by the herbicide often exacerbated by an insecticide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbi- cide-to-antidote ratio ranging from 1:25-to-60:1 (preferably 1:5-to-30:1) parts by weight may be employed, although much higher rates of antidote may be used, e.g., 1:100–1:300 parts by weight of herbicide-to-antidote. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.03 to about 12 kilograms/hectare, but rates as low as 0.004 kg/ha may be used effectively. The preferred range of rate of application is from about 0.1 to about 10 kg/ha. Preferably, antidote application rates range from about 8–10 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

Any biocides used will be applied at rates recommended by the supplier/manufacturer.

The application of the antidote can be made directly to the seed before planting. In this practice, a quantity of crop seed is first coated with the antidote. The coated seed is thereafter planted. The herbicide may be applied to the soil before or after the coated seed is planted.

In field applications, the herbicide and antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as biocide(s), diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The sequence of addition of chemicals is optional, but in common applications, the antidote may be applied to the seed or soil followed by application of the herbicide of Formula I alone or in admixture with a co-herbicide. Various sequential modifications of application of the chemicals conventional in the art are contemplated.

Evaluations of safening activity of representative herbicidal and antidote compounds of this invention were carried out using the specific procedures described below in greenhouse and field testing. Measurements of biological response as reported in the tables were made by visual observation and the degree of plant injury recorded in terms of percent injury.

Listed below are the names of various antidotal compounds tested herein and representative ones for which data are reported in the tables.

| Antidote No. | Nomenclature |
| --- | --- |
| 1 | Acetamide, N,N-bis(2-propenyl)-α,α-dichloro, (common name "dichlormid"; Code No. R-25788), |
| 2 | 1H, 3H-Naphtho [1,8-cd]pyran-1,3-dione, |
| 3 | cis/Trans-piperazine, 1,4-bis(dichloro-1,4-acetyl)-2,5-dimethyl-, |
| 4 | 5-Thiazolecarboxylic acid, 2-chloro-4-(trifluoromethyl)-, (common name "flurazole"), |
| 5 | Oxazolidine, 3-(dichloroacetyl)-2,2,5-trimethyl-, (Code No. R-29148), |
| 6 | Benzeneacetonitrile, α-{[(1,3-dioxo-lan-2-yl)methoxy]imino}-, (common name "oxabetrinil"), |
| 7 | 1-Oxa-4-azaspiro[4,5]decane, 4-(dichloro-acetyl)-, (Code No. AD-67), |
| 8 | 1,5-Diazacyclononane, 1,5-bis(dichloro-acetyl)-, |
| 9 | 1-Azaspiro[4,4]nonane, 1-(dichloro-acetyl)-, |
| 10 | Acetamide, 2,2-dichloro-N-(1,3-dioxo-lan-2-ylmethyl)-N-2-propenyl-(Code No. PPG-1292), |
| 11 | Oxazolidine, 3-(dichloroacetyl)-2,2-di-methyl-5-(2-thienyl)-, |
| 12 | Ethanone, 2,2-dichloro-1-(1,2,3,4-tetra-hydro-1-methyl]-2-isoquinolinyl)-, |
| 13 | 1,3-Dioxolane, 2-(dichloromethyl)-2-methyl-, (Code No. MG-191), |
| 14 | 5-Dichloroacetyl-3,3,6-trimethyl-9-oxo-1,5-diazabicyclo[4.3.0]nonane, (Code No. BAS-145138), |
| 15 | Oxazolidine, 3-(dichloroacetyl)-5-(2-furanyl)-2,2-dimethyl, |

-continued

| Antidote No. | Nomenclature |
|---|---|
| 16 | Pyridine, 3-[3-[(dichloroacetyl)-2,2-dimethyl-5-oxazolidinyl]-, |
| 17 | 4-(Dichloroacetyl)-3,4-dihydro-3-methyl-2H-1,4-benzoxazine (common name "benoxychlor"; Code No. CGA-154281), |
| 18 | Acetic acid, (diphenylmethoxy)- sodium salt, hemihydrate, |
| 19 | Acetic acid, (diphenylmethoxy)-, |
| 20 | Acetic acid, (diphenylmethoxy)-, methyl ester, (Code No. MON-7400), |
| 21 | Ethanethioic acid, 2-(diphenylmethoxy)-5-ethyl ester. |

Listed below are the names of various herbicidal compounds tested herein and representative ones for which data are reported in the tables.

| Herbicide No. | Nomenclature |
|---|---|
| 1 | N-[(4,6-dimethoxypyridin-2-yl)aminocarbonyl]-3-chloro-4-methoxycarbonyl 1-methylpyrazole-5-sulfonamide (Code No. A-84110; also NC-319), |
| 2 | N-[(4,6-dimethoxypyridin-2-yl)aminocarbonyl]-3-chloro-4-ethoxycarbonyl 1-methylpyrazole-5-sulfonamide (Code No. A-841065; also NC-319-EX), |
| 3 | N-[(4,6-dimethoxypyrimidin-2-yl)aminocarbonyl]-4-ethoxycarbonyl 1-methylpyrazole-5-sulfonamide (Code No. NC-311), |
| 4 | Ethyl dipropylthiocarbamate (common name "EPTC"), |
| 5 | 2-Chloro-N-isopropylacetanilide (common name "propachlor"), |
| 6 | 2-Chloro-N-(ethoxymethyl)-6'-ethyl-o-acetoluidide (common name "acetochlor"), |
| 7 | 2-Chloro-2',6'-diethyl-N-(methoxymethyl)-acetanilide (common name "alachlor"), |
| 8 | 3,6-Dichloro-2-methoxybenzoic acid (common name "dicamba"), |
| 9 | 2-Chloro-2',6'-diethyl-N-(butoxymethyl)-acetanilide (common name "butachlor"), |
| 10 | S-ethyl-diisobutylthiocarbamade (common name "butylate"), |
| 11 | S-propyl dipropylthiocarbamate (common name "vernolate"), |
| 12 | 2-Chloro-N-(2-methoxy-1-methylethyl)-6'-ethyl-o-acetotoluidide (common name "metolachlor"), |
| 13 | 2-Chloro-N-(2-n-propoxyethyl)-2',6'-diethylacetanilide (common name "pretilachlor"), |
| 14 | 2-Chloro-2',6'-dimethyl-N-(1-pyrazol-1-yl-methyl)acetanilide (common name "metazachlor"). |

Greenhouse tests with the above compounds were conducted according to general Procedures I–II described below, with modifications noted in the relevant examples.

Procedure I

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide +antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers the cover layer of the first container was not treated with herbicide or antidote. The cover layer of the second container had a measured quantity of herbicide alone incorporated therein.

The containers were then placed on a bench in a greenhouse and sub-irrigated as required for the duration of the test. Plant response was observed at various times, but usually about three weeks after initial treatment; variations will be noted in the examples. Plant response is measured in terms of percent injury. Antidote efficacy is indicated as the difference in plant injury by the herbicide(s) without the antidote and with the antidote.

Procedure II.

This procedure is the same as Procedure I, but modified in the manner that after incorporation of the chemicals (herbicide and antidote) the containers with the covered seedbed were treated with an initial overhead irrigation equivalent to 0.6 cm rainfall, then subsequently sub-irrigated as required on greenhouse benches.

In a series of greenhouse tests, a variety of antidotal compounds were tested for their efficacy against various herbicides. In one series of tests (Examples 1–4), the antidotal compounds were tested against a representative and preferred herbicidal compound according to Formula I with no co-herbicidal compound being present. In another series of tests (Examples 5–22), the Formula I compound was combined with various co-herbicidal compounds from different classes of chemistry to ascertain whether the antidotal effect was maintained with such combination of herbicides.

In the series of greenhouse tests described below, for routine screening purposes the herbicide/antidote compositions were tested in crop/weed combinations involving corn as the crop and either or both of the weeds barnyardgrass (*Echinochloa crusgalli*), a monocotyledonous weed, and velvetleaf (*Abutilon theophrasti*), a dicotyledonous weed. In the tables below, these weeds are indicated by the symbols "BYG" and "VL", respectively.

EXAMPLE 1

This example was designed to investigate the antidotal efficacy of a plurality of antidotes against Herbicide No. 1 in corn in the presence of barnyard grass and velvetleaf. The antidotes used in this example were Antidote Nos. 1–10, 12, 13 and 15.

The test in this example was conducted as described above for Procedure II. The antidotes were applied to the soil cover layer by pipet after spraying on the herbicide followed by incorporation and simulated rain.

TABLE 1

| Herb. No. 1 Kg/Ha | Antidote No. | Rate Kg/ha | % Injury | | |
|---|---|---|---|---|---|
| | | | Corn | BYG | VL |
| 0.56 | — | — | 40 | 75 | 95 |
| 0.14 | — | — | 5 | 50 | 85 |

TABLE 1-continued

| Herb. No. 1 Kg/Ha | Antidote No. | Rate Kg/ha | % Injury Corn | BYG | VL |
|---|---|---|---|---|---|
| 0.56 | 15 | 8.96 | 10 | 55 | 70 |
| 0.14 | " | " | 15 | 40 | 65 |
| 0.56 | " | 2.24 | 5 | 55 | 80 |
| 0.14 | " | " | 5 | 45 | 65 |
| 0.56 | 7 | 8.96 | 15 | 55 | 90 |
| 0.14 | " | " | 5 | 35 | 75 |
| 0.56 | " | 2.24 | 30 | 75 | 90 |
| 0.14 | " | " | 0 | 55 | 60 |
| 0.56 | 1 | 8.96 | 0 | 85 | 90 |
| 0.14 | " | " | 20 | 50 | 85 |
| 0.56 | " | 2.24 | 15 | 75 | 97 |
| 0.14 | " | " | 10 | 60 | 75 |
| 0.56 | 5 | 8.96 | 10 | 65 | 80 |
| 0.14 | " | " | 5 | 40 | 70 |
| 0.56 | " | 2.24 | 15 | 80 | 90 |
| 0.14 | " | " | 10 | 50 | 70 |
| 0.56 | 10 | 8.96 | 10 | 50 | 65 |
| 0.14 | " | " | 20 | 40 | 80 |
| 0.56 | — | 2.24 | 5 | 65 | 80 |
| 0.14 | " | " | 20 | 50 | 65 |
| 0.56 | 3 | 8.96 | 20 | 65 | 85 |
| 0.14 | " | " | 5 | 40 | 80 |
| 0.56 | " | 2.24 | 5 | 65 | 95 |
| 0.14 | " | " | 5 | 45 | 75 |
| 0.56 | 12 | 8.96 | 25 | 50 | 85 |
| 0.14 | " | " | 15 | 50 | 65 |
| 0.56 | " | 2.24 | 10 | 60 | 95 |
| 0.14 | " | " | 5 | 30 | 80 |
| 0.56 | 9 | 8.96 | 0 | 65 | 75 |
| 0.14 | " | " | 5 | 40 | 55 |
| 0.56 | " | 2.24 | 10 | 60 | 65 |
| 0.14 | " | " | 5 | 35 | 60 |
| 0.56 | 8 | 8.96 | 10 | 60 | 85 |
| 0.14 | 8 | 8.96 | 5 | 20 | 65 |
| 0.56 | " | 2.24 | 20 | 70 | 85 |
| 0.14 | " | " | 5 | 40 | 70 |
| 0.56 | 2 | 8.96 | 10 | 35 | 85 |
| 0.14 | " | " | 10 | 15 | 65 |
| 0.56 | " | 2.24 | 10 | 35 | 85 |
| 0.14 | " | " | 5 | 40 | 55 |
| 0.56 | 13 | 8.96 | 20 | 85 | 95 |
| 0.14 | " | " | 5 | 35 | 75 |
| 0.56 | " | 2.24 | 25 | 60 | 65 |
| 0.14 | " | " | 15 | 25 | 55 |
| 0.56 | 4 | 8.96 | 10 | 60 | 70 |
| 0.14 | " | " | 10 | 45 | 60 |
| 0.56 | " | 2.24 | 5 | 50 | 80 |
| 0.14 | " | " | 0 | 20 | 65 |
| 0.56 | 6 | 8.96 | 20 | 30 | 85 |
| 0.14 | " | " | 10 | 15 | 70 |
| 0.56 | " | 2.24 | 10 | 30 | 65 |
| 0.14 | " | " | 15 | 15 | 55 |
| Control | | | 0 | 0 | 0 |
| Control | | | 0 | 0 | 0 |

Referring to the data in Table 1, it is noted that all of antidotes tested against Herbicide No. 1 at 0.56 kg/ha PPI (preplant incorporated) reduced injury to the corn from 40% (without an antidote) to levels of from 0% to a maximum of 30% injury. In this test, the best safening effect across quadruple treatments was achieved by Antidote No. 9. At herbicide:antidote ratios of 1:16 all but four antidotes (Nos. 3, 6, 12 and 13) provided commercially-acceptable protection (i.e., no greater than 15% injury) for the corn. However, decreasing the herbicide:antidote ratio to 1:57 provided commercial-level safening for all antidotes, except Antidotes 1 and 10, which were only slightly more injurious to corn at 20% injury.

EXAMPLE 2

In this example, a plurality of dichloroacetamide antidotes were tested for their safening efficacy against Herbicide No. 1 in corn, using Procedure II. In this test the weed was velvetleaf; barnyardgrass was not present in this test. Test results are shown in Table 2.

TABLE 2

| Herb. No. 1 Kg/ha | Antidote No. | Rate Kg/ha | % Injury Corn | VL |
|---|---|---|---|---|
| 0.14 | — | — | 10 | 95 |
| 0.56 | — | — | 55 | 85 |
| 2.24 | — | — | 80 | 95 |
| 0.14 | 1 | 0.56 | 10 | 100 |
| 0.56 | 1 | " | 10 | 95 |
| 2.24 | 1 | " | 30 | 100 |
| 0.14 | 1 | 2.24 | 10 | 90 |
| 0.56 | 1 | " | 25 | 85 |
| 2.24 | 1 | " | 40 | 100 |
| 0.14 | 3 | 0.56 | 15 | 90 |
| 0.56 | 3 | " | 10 | 90 |
| 2.24 | 3 | " | 40 | 90 |
| 0.14 | 3 | 2.24 | 10 | 90 |
| 0.56 | 3 | " | 10 | 90 |
| 2.24 | 3 | " | 50 | 100 |
| 0.14 | 5 | 0.56 | 10 | 95 |
| 0.56 | 5 | " | 8 | 95 |
| 2.24 | 5 | " | 30 | 100 |
| 0.14 | 5 | 2.24 | 25 | 90 |
| 0.56 | 5 | " | 15 | 95 |
| 2.24 | 5 | " | 20 | 100 |
| 0.14 | 7 | 0.56 | 5 | 95 |
| 0.56 | 7 | " | 15 | 85 |
| 2.24 | 7 | " | 40 | 95 |
| 0.14 | 7 | 2.24 | 10 | 75 |
| 0.56 | 7 | " | 5 | 90 |
| 2.24 | 7 | " | 50 | 95 |
| 0.14 | 10 | 0.56 | 5 | 95 |
| 0.56 | 10 | " | 10 | 65 |
| 2.24 | 10 | " | 40 | 90 |
| 0.14 | 10 | 2.24 | 10 | 95 |
| 0.56 | 10 | " | 15 | 95 |
| 2.24 | 10 | " | 20 | 95 |
| 0.14 | 12 | 0.56 | 5 | 100 |
| 0.56 | 12 | " | 20 | 95 |
| 2.24 | 12 | " | 35 | 95 |
| 0.14 | 12 | 2.24 | 10 | 80 |
| 0.56 | 12 | " | 5 | 85 |
| 2.24 | 12 | " | 15 | 95 |
| 0.14 | 14 | 0.56 | 5 | 95 |
| 0.56 | 14 | " | 5 | 80 |
| 2.24 | 14 | " | 20 | 95 |
| 0.14 | 14 | 2.24 | 0 | 60 |
| 0.56 | 14 | " | 5 | 90 |
| 2.24 | 14 | " | 20 | 95 |
| 0.14 | 15 | 0.56 | 5 | 75 |
| 0.56 | 15 | " | 10 | 90 |
| 2.24 | 15 | " | 10 | 95 |
| 0.14 | 15 | 2.24 | 10 | 65 |
| 0.56 | 15 | " | 15 | 95 |
| 2.24 | 15 | " | 10 | 90 |

In the test data shown in Table 2, it is seen that overall Antidote No. 15 provided the most safening and commercial-level protection for corn, at all ratios tested, followed in order by Antidote Nos. 14, 12, 7 and 10. In general, the rate effect of higher antidote: herbicide ratios produced the greatest safening effect.

EXAMPLE 3

This example details the results of tests with Antidote Nos. 12, 15 and 16 to safen Herbicide No. 1 over application rates ranging from 4.48 kg/ha down to 0.56 kg/ha, in corn in the presence of barnyardgrass. Procedure I described above was used in these tests. Results of these tests are set forth in Table 3.

TABLE 3

| Herb. No. 1 Kg/ha | Antidote No. | Rate Kg/ha | % Injury Corn | BYG |
|---|---|---|---|---|
| 4.48 | — | — | 60 | 75 |
| 2.24 | — | — | 38 | 70 |
| 1.12 | — | — | 13 | 70 |
| 0.56 | — | — | 7 | 50 |
| 4.48 | 11 | 0.56 | 50 | 80 |
| 2.24 | 11 | " | 30 | 75 |
| 1.12 | 11 | " | 5 | 80 |
| 0.56 | 11 | " | 15 | 70 |
| 4.48 | 11 | 2.24 | 30 | 80 |
| 2.24 | 11 | " | 0 | 30 |
| 1.12 | 11 | " | 0 | 15 |
| 0.56 | 11 | " | 0 | 20 |
| 4.48 | 11 | 8.96 | 5 | 50 |
| 2.24 | 11 | " | 0 | 0 |
| 1.12 | 11 | " | 0 | 0 |
| 0.56 | 11 | " | 0 | 0 |
| — | 11 | " | 15 | 0 |
| 4.48 | 15 | 0.56 | 0 | 75 |
| 2.24 | 15 | " | 15 | 60 |
| 1.12 | 15 | " | 0 | 75 |
| 0.56 | 15 | " | 0 | 50 |
| 4.48 | 15 | 2.24 | 5 | 70 |
| 2.24 | 15 | " | 0 | 70 |
| 1.12 | 15 | " | 0 | 60 |
| 0.56 | 15 | " | 0 | 35 |
| 4.48 | 15 | 8.96 | 0 | 80 |
| 2.24 | 15 | " | 0 | 50 |
| 1.12 | 15 | " | 0 | 60 |
| 0.56 | 15 | " | 0 | 10 |
| — | 15 | " | 0 | 0 |
| 4.48 | 16 | 0.56 | 5 | 75 |
| 2.24 | 16 | " | 5 | 85 |
| 1.12 | 16 | " | 0 | 70 |
| 0.56 | 16 | " | 0 | 65 |
| 4.48 | 16 | 2.24 | 5 | 80 |
| 2.24 | 16 | " | 0 | 90 |
| 1.12 | 16 | " | 0 | 80 |
| 0.56 | 16 | " | 0 | 60 |
| 4.48 | 16 | 8.96 | 5 | 95 |
| 2.24 | 16 | " | 0 | 80 |
| 1.12 | 16 | " | 0 | 85 |
| 0.56 | 16 | " | 0 | 50 |
| — | 16 | " | 0 | 0 |

It is seen from the data in Table 3 that each of the tested antidotes provided excellent protection for corn, especially Antidote Nos. 15 and 16 over a variety of antidote:herbicide ratios. Moreover, at selected herbicide:antidote ratios, the observed corn protection was accompanied by generally comparable-to-enhanced weed control vis-a-vis that for the unsafened herbicide, an unexpected synergistic effect.

Table 4

This example describes tests with Antidote Nos. 15 and 16 to safen Herbicide No. 1 according to Procedure I using corn and the weeds barnyardgrass and velvetleaf as the test plants. Test results (averages of two replicates) are shown in Table 4.

TABLE 4

| Herb. No. 1 Kg/Ha | Antidote No. | Rate Kg/ha | % Injury Corn | BYG | VL |
|---|---|---|---|---|---|
| 6.72 | — | — | 90 | 905 | 90 |
| 4.48 | — | — | 85 | 80 | 90 |
| 6.72 | 15 | 0.56 | 35 | 90 | 95 |
| 4.48 | 15 | " | 10 | 95 | 95 |
| 6.72 | 15 | 2.24 | 50 | 90 | 95 |
| 4.48 | 15 | " | 13 | 90 | 95 |
| 6.72 | 16 | 0.56 | 35 | 95 | 95 |
| 4.48 | 16 | " | 70 | 95 | 95 |
| 6.72 | 16 | 2.24 | 30 | 95 | 95 |
| 4.48 | 16 | " | 15 | 95 | 95 |

The data in Table 4 show that both Antidote Nos. 15 and 16 provided substantial safening of Herbicide No. 1, which by itself essentially destroyed the corn crop. Enhanced safening of the herbicide was achieved by a combination of reduced rates of application of the herbicide and/or increased rates of application of the antidotes. For both antidotes commercial-level protection of corn against Herbicide No. 1 was achieved at the herbicide application rate of 4.48 kg/ha and antidote application rate of 2.24 kg/ha, while maintaining essentially complete weed control.

As noted earlier, the tests conducted in Examples 1–4 were to determine the antidotal efficacy of a plurality of antidotes against a typical, representative herbicide according to Formula I. In the following Examples, tests were conducted to determine the efficacy of various antidotes against a combination of said herbicide, together with various co-herbicidal compounds.

EXAMPLE 5

In the tests described in this example, the same procedure described in Example 4 was performed simultaneously therewith and under the same conditions, except that a co-herbicide, alachlor, was included in the same composition with Herbicide No. 1 and Antidote Nos. 15 and 16. Alachlor (Herbicide No. 7 herein) is the active ingredient in the commercial product LASSO® herbicide. Test results are reported in Table 5.

TABLE 5

| Herbicide Kg/ha | | Antidote Kg/ha | | % Injury | | |
|---|---|---|---|---|---|---|
| No. 1 | No. 7 | No. | Rate | Corn | BYG | VL |
| 6.72 | — | — | — | 90 | 90 | 90 |
| 4.48 | — | — | — | 85 | 80 | 90 |
| 6.72 | 2.24 | — | — | 95 | 100 | 98 |
| 4.48 | " | — | — | 95 | 100 | 98 |
| 6.72 | 0.56 | — | — | 93 | 99 | 98 |
| 4.48 | " | — | — | 95 | 99 | 98 |
| 6.72 | — | 15 | 0.56 | 35 | 90 | 95 |
| 4.48 | — | 15 | " | 10 | 95 | 95 |
| 6.72 | — | 15 | 2.24 | 50 | 90 | 95 |
| 4.48 | — | 15 | " | 13 | 90 | 95 |
| 6.72 | 2.24 | 15 | 0.56 | 45 | 100 | 99 |
| 4.48 | " | 15 | " | 30 | 100 | 98 |
| 6.72 | 0.56 | 15 | " | 25 | 99 | 95 |
| 4.48 | " | 15 | " | 23 | 99 | 95 |
| 6.72 | 2.24 | 15 | 2.24 | 50 | 100 | 95 |
| 4.48 | " | 15 | " | 23 | 100 | 95 |
| 6.72 | 0.56 | 15 | " | 25 | 99 | 99 |
| 4.48 | " | 15 | " | 40 | 95 | 95 |
| 6.72 | — | 16 | 0.56 | 35 | 95 | 95 |
| 4.48 | — | 16 | " | 70 | 95 | 95 |
| 6.72 | — | 16 | 2.24 | 30 | 95 | 95 |
| 4.48 | — | 16 | " | 15 | 95 | 95 |
| 6.72 | 2.24 | 16 | 0.56 | 80 | 100 | 98 |
| 4.48 | " | 16 | " | 53 | 100 | 98 |
| 6.72 | 0.56 | 16 | " | 43 | 95 | 98 |

TABLE 5-continued

| Herbicide Kg/ha | | Antidote Kg/ha | | % Injury | | |
|---|---|---|---|---|---|---|
| No. 1 | No. 7 | No. | Rate | Corn | BYG | VL |
| 4.48 | " | 16 | " | 48 | 100 | 95 |
| 6.72 | 2.25 | 16 | 2.24 | 55 | 100 | 99 |
| 4.48 | " | 16 | " | 40 | 100 | 98 |
| 6.72 | 0.56 | 16 | " | 55 | 100 | 95 |
| 4.48 | " | 16 | " | 18 | 100 | 95 |

As noted from the above data in Table 5, both Antidotes 15 and 16 exhibited substantial safening of corn from the herbicidal effects of both Herbicide Nos. 1 and 7, while maintaining complete control of both weeds. Injury to corn by 4.48 kg/ha of Herbicide No. 1 was reduced from 85% to 10% and 13%, respectively, by the antidotal action of Antidote No. 15 at 0.56 and 2.24 kg/ha, with no alachlor present. Even so, at all rates at which Herbicide No. 7 was present, the minimum reduction in injury was 45% (i.e., from 95% at 2.24 kg/ha of Herbicide No. 7 with both rates of 6.72 and 4.48 kg/ha of Herbicide No. 1 when no antidote was present to 50% injury when 2.24 kg/ha of Antidote No. 1 was present).

Similarly, but to a lesser degree, Antidote No. 16 was effective to reduce combined injury by the two herbicides to a substantial degree, particularly at increased ratios of antidote:herbicide concentration.

EXAMPLE 6

This example was designed to investigate the antidotal efficacy of a plurality of antidotal compounds against a composition comprising Herbicide No. 1 in combination with Herbicide No. 7 (alachlor). The antidotal compounds used herein were Nos. 1, 2, 7, 13 and 15.

In this example, Procedure II described above was followed. The data from the tests in this example is shown in Table 6 and represents averages of duplicate replications.

TABLE 6

| Herbicide Kg/ha | | Antidote Kg/ha | | % Injury | | |
|---|---|---|---|---|---|---|
| No. 1 | No. 7 | No. | Rate | Corn | BYG | VL |
| 0.56 | 4.48 | — | — | 30 | 100 | 85 |
| 0.14 | " | — | — | 20 | 100 | 70 |
| 0.56 | " | 15 | 8.96 | 15 | 100 | 95 |
| 0.14 | " | 15 | " | 10 | 100 | 65 |
| 0.56 | " | 15 | 2.24 | 15 | 100 | 90 |
| 0.14 | " | 15 | " | 20 | 100 | 80 |
| 0.56 | " | 7 | 8.96 | 5 | 100 | 90 |
| 0.14 | " | 7 | " | 10 | 100 | 75 |
| 0.56 | " | 7 | 2.24 | 10 | 100 | 90 |
| 0.14 | " | 7 | " | 0 | 100 | 75 |
| 0.56 | " | 1 | 8.96 | 5 | 100 | 85 |
| 0.14 | " | 1 | " | 0 | 100 | 80 |
| 0.56 | " | 1 | 2.24 | 15 | 100 | 80 |
| 0.14 | " | 1 | " | 10 | 100 | 75 |
| 0.56 | " | 2 | 8.96 | 15 | 100 | 90 |
| 0.14 | " | 2 | " | 15 | 100 | 75 |
| 0.56 | " | 2 | 2.24 | 15 | 100 | 80 |
| 0.14 | " | 2 | " | 0 | 100 | 70 |
| 0.56 | " | 13 | 8.96 | 15 | 100 | 90 |
| 0.14 | " | 13 | " | 0 | 100 | 65 |
| 0.56 | " | 13 | 2.24 | 5 | 100 | 90 |
| 0.14 | " | 13 | " | 0 | 100 | 75 |
| 0.56 | — | — | — | 25 | 70 | 60 |
| 0.14 | — | — | — | 5 | 20 | 40 |

TABLE 6-continued

| Herbicide Kg/ha | | Antidote Kg/ha | | % Injury | | |
|---|---|---|---|---|---|---|
| No. 1 | No. 7 | No. | Rate | Corn | BYG | VL |
| — | 4.48 | — | — | 10 | 100 | 25 |
| Control | | | | 0 | 0 | 0 |

Reference to the data in Table 6 shows that all antidotes in the test protected corn from a combination of Herbicides 1 and 7 applied PPI. Antidote No. 13 provided the best safening effect across four treatments. The best corn protection in this test was provided by Antidotes 7 and 1 applied at the highest test rate of herbicide and antidote. Excellent control of barnyardgrass and suppression-to-good control of velvetleaf was maintained while providing the reduced corn injury by the herbicides.

EXAMPLE 7

The tests in this example followed the same procedure and antidotes used in Example 6. However, Herbicide No. 12 (metolachlor) was used as the coherbicide with Herbicide No. 1. Test results are shown in Table 7.

TABLE 7

| Herbicide Kg/ha | | Antidote Kg/ha | | % Injury | | |
|---|---|---|---|---|---|---|
| No. 1 | No. 12 | No. | Rate | Corn | BYG | VL |
| 0.56 | 3.36 | — | — | 30 | 100 | 85 |
| 0.14 | " | — | — | 20 | 100 | 70 |
| 0.56 | " | 15 | 8.96 | 15 | 100 | 70 |
| 0.14 | " | 15 | " | 10 | 100 | 65 |
| 0.56 | " | 15 | 2.24 | 15 | 100 | 75 |
| 0.14 | " | 15 | " | 0 | 100 | 70 |
| 0.56 | " | 7 | 8.96 | 15 | 100 | 85 |
| 0.14 | " | 7 | " | 10 | 100 | 65 |
| 0.56 | " | 7 | 2.24 | 20 | 100 | 85 |
| 0.14 | " | 7 | " | 10 | 100 | 70 |
| 0.56 | " | 1 | 8.96 | 10 | 100 | 80 |
| 0.14 | " | 1 | " | 0 | 100 | 75 |
| 0.56 | " | 1 | 2.24 | 0 | 100 | 85 |
| 0.14 | " | 1 | " | 0 | 100 | 70 |
| 0.56 | " | 2 | 8.96 | 15 | 100 | 85 |
| 0.14 | " | 2 | " | 0 | 100 | 75 |
| 0.56 | " | 2 | 2.24 | 10 | 100 | 80 |
| 0.14 | " | 2 | " | 0 | 100 | 75 |
| 0.56 | " | 13 | 8.96 | 10 | 100 | 85 |
| 0.14 | " | 13 | " | 0 | 100 | 80 |
| 0.56 | " | 13 | 2.24 | 10 | 100 | 85 |
| 0.14 | " | 13 | " | 0 | 100 | 75 |
| 0.56 | " | — | — | 10 | 75 | 75 |
| 0.14 | " | — | — | 0 | 35 | 60 |
| — | 3.36 | — | — | 0 | 100 | 20 |
| Control | — | — | — | 0 | 0 | 0 |

As will be noted in the data in Table 7, all antidotes provided safening of the corn while maintaining substantial weed control or suppression in compositions comprising the two test herbicides. All of the safener treatments provided commercially-acceptable corn safety at all test rates, except for Antidote No. 7. At 0.56 kg/ha of Herbicide No. 1 plus 3.36 kg/ha of Herbicide No. 12 and 2.24 kg/ha of Antidote No. 7, corn injury at 20% was slightly higher than commercially desirable. Antidote No. 1 provided the best safening effect across four treatments. Control of barnyardgrass was total, while that for velvetleaf was good to excellent.

EXAMPLE 8

In this test, the efficacy of the same five antidotes used in Examples 6 and 7 was investigated in compositions comprising Herbicide No. 1 and as a co-herbicide, butachlor (Herbicide No. 9), active ingredient in MACHETE® herbicide, a leading commercial rice herbicide. The test procedure used in this example was the same as that in Examples 6 and 7. Test results are shown in Table 8.

TABLE 8

| Herbicide Kg/ha | | Antidote Kg/ha | | % Injury | | |
|---|---|---|---|---|---|---|
| No. 1 | No. 9 | No. | Rate | Corn | BYG | VL |
| 0.56 | 2.24 | — | — | 65 | 100 | 85 |
| 0.14 | " | — | — | 25 | 100 | 70 |
| 0.56 | " | 15 | 8.96 | 10 | 97 | 75 |
| 0.14 | " | 15 | " | 15 | 98 | 70 |
| 0.56 | " | 15 | 2.24 | 10 | 95 | 80 |
| 0.14 | " | 15 | " | 20 | 99 | 85 |
| 0.56 | " | 7 | 8.96 | 20 | 99 | 65 |
| 0.14 | " | 7 | " | 10 | 99 | 65 |
| 0.56 | " | 7 | 2.24 | 25 | 99 | 75 |
| 0.14 | " | 7 | " | 5 | 97 | 70 |
| 0.56 | " | 1 | 8.96 | 15 | 99 | 80 |
| 0.14 | " | 1 | " | 10 | 99 | 70 |
| 0.56 | " | 1 | 2.24 | 20 | 98 | 85 |
| 0.14 | " | 1 | " | 20 | 99 | 70 |
| 0.56 | " | 2 | 8.96 | 20 | 98 | 80 |
| 0.14 | " | 2 | " | 15 | 99 | 75 |
| 0.56 | " | 2 | 2.24 | 25 | 99 | 90 |
| 0.14 | " | 2 | " | 15 | 99 | 70 |
| 0.56 | " | 13 | 8.96 | 30 | 100 | 85 |
| 0.14 | " | 13 | " | 10 | 99 | 80 |
| 0.56 | " | 13 | 2.24 | 45 | 99 | 85 |
| 0.14 | " | 13 | " | 25 | 99 | 75 |
| 0.56 | — | — | — | 60 | 93 | 85 |
| 0.14 | — | — | — | 10 | 55 | 70 |
| — | 2.24 | — | — | 5 | 99 | 25 |
| Control | | | | 0 | 0 | 0 |

In the above data, Herbicide No. 1 at 0.56 kg/ha plus Herbicide No. 9 at 2.24 kg/ha caused 65% corn injury without an antidote. The addition of an antidote reduced corn injury substantially in all cases; many combinations and rates of the tested composition reduced corn injury to commercially-acceptable levels, while maintaining or enhancing weed control or suppression. The best safening effect across all four treatments was achieved by Antidote No. 15.

EXAMPLE 9

In this example the safening effect on a composition comprising Herbicide No. 1 and another leading rice herbicide, i.e., Herbicide No. 13, was investigated using the same antidotes and test procedure described in the preceding example. Herbicide No. 13 is pretilachlor, active ingredient used in the commercial rice herbicides RIFIT®, SOFIT® and SOFIT® SUPER. Test results are shown in Table 9.

TABLE 9

| Herbicide Kg/ha | | Antidote Kg/ha | | % Injury | | |
|---|---|---|---|---|---|---|
| No. 1 | No. 13 | No. | Rate | Corn | BYG | VL |
| 0.56 | 2.24 | — | — | 65 | 100 | 90 |
| 0.14 | " | — | — | 10 | 100 | 70 |
| 0.56 | " | 15 | 8.96 | 5 | 100 | 75 |
| 0.14 | " | 15 | " | 0 | 100 | 90 |
| 0.56 | " | 15 | 2.24 | 15 | 99 | 85 |
| 0.14 | " | 15 | " | 5 | 100 | 60 |
| 0.56 | " | 7 | 8.96 | 25 | 100 | 85 |
| 0.14 | " | 7 | " | 0 | 100 | 75 |
| 0.56 | " | 7 | 2.24 | 30 | 100 | 85 |
| 0.14 | " | 7 | " | 10 | 100 | 80 |
| 0.56 | " | 1 | 8.96 | 10 | 100 | 85 |
| 0.14 | " | 1 | " | 0 | 100 | 75 |
| 0.56 | " | 1 | 2.24 | 5 | 100 | 85 |
| 0.14 | " | 1 | " | 0 | 100 | 75 |
| 0.56 | " | 2 | 8.96 | 20 | 100 | 80 |
| 0.14 | " | 2 | " | 5 | 100 | 75 |
| 0.56 | " | 2 | 2.24 | 20 | 100 | 85 |
| 0.14 | " | 2 | " | 5 | 100 | 80 |
| 0.56 | " | 13 | 8.96 | 20 | 100 | 90 |
| 0.14 | " | 13 | " | 0 | 100 | 75 |
| 0.56 | " | 13 | 2.24 | 25 | 100 | 90 |
| 0.14 | " | 13 | " | 10 | 100 | 70 |
| 0.56 | " | — | — | 20 | 75 | 80 |
| 0.14 | " | — | — | 5 | 60 | 70 |
| — | 2.24 | — | — | 0 | 100 | 5 |
| Control | | | | 0 | 0 | 0 |

Herbicide Nos. 1 at 0.56 kg/ha and 13 at 2.24 kg/ha in combination caused 65% injury to corn. However, that corn injury was greatly reduced by each of the five antidotes in the test. The best safening effect across four treatments was achieved by Antidote No. 1, which together with Antidote No. 15 provided commercial-level safening of corn against the two herbicides in all herbicide:antidote combinations. All treatments resulted in complete control of barnyardgrass and substantial control or suppression of velvetleaf.

EXAMPLE 10

In this test, the safening effect of various antidotes on the herbicidal combination of Herbicide No. 1 and another α-chloroacetanilide co-herbicide, propachlor, (Herbicide No. 5) was investigated. Propachlor is the active ingredient in the commercial herbicide RAMROD®. Procedure II was also used in this test as in the preceding example. Test results are shown in Table 10.

TABLE 10

| Herbicide Kg/ha | | Antidote Kg/ha | | % Injury | | |
|---|---|---|---|---|---|---|
| No. 1 | No. 5 | No. | Rate | Corn | BYG | VL |
| 0.56 | 4.48 | — | — | 70 | 100 | 80 |
| 0.14 | " | — | — | 5 | 100 | 70 |
| 0.56 | " | 15 | 8.96 | 10 | 85 | 75 |
| 0.14 | " | 15 | " | 0 | 90 | 80 |
| 0.56 | " | 15 | 2.24 | 10 | 93 | 80 |
| 0.14 | " | 15 | " | 0 | 98 | 70 |
| 0.56 | " | 7 | 8.96 | 25 | 96 | 80 |
| 0.14 | " | 7 | " | 10 | 98 | 75 |
| 0.56 | " | 7 | 2.24 | 40 | 98 | 95 |
| 0.14 | " | 7 | " | 10 | 99 | 70 |
| 0.56 | " | 1 | 8.96 | 0 | 99 | 80 |
| 0.14 | " | 1 | " | 0 | 99 | 70 |
| 0.56 | " | 1 | 2.24 | 15 | 98 | 70 |
| 0.14 | " | 1 | " | 10 | 99 | 75 |
| 0.56 | " | 2 | 8.96 | 25 | 99 | 80 |
| 0.14 | " | 2 | " | 10 | 99 | 80 |
| 0.56 | " | 2 | 2.24 | 15 | 99 | 75 |
| 0.14 | " | 2 | " | 15 | 100 | 60 |
| 0.56 | " | 13 | 8.96 | 10 | 98 | 75 |

TABLE 10-continued

| Herbicide Kg/ha | | Antidote Kg/ha | | % Injury | | |
|---|---|---|---|---|---|---|
| No. 1 | No. 5 | No. | Rate | Corn | BYG | VL |
| 0.14 | " | 13 | " | 15 | 97 | 70 |
| 0.56 | " | 13 | 2.24 | 45 | 99 | 80 |
| 0.14 | " | 13 | " | 0 | 98 | 70 |
| 0.56 | — | — | — | 30 | 80 | 75 |
| 0.14 | — | — | — | 20 | 75 | 70 |
| — | 4.48 | — | — | 0 | 100 | 15 |
| Control | | | | 0 | 0 | 0 |

Significant reduction of corn injury by the herbicides composition was achieved by all antidotes tested. Antidote No. 15 achieved the best safening effect, followed closely by Antidote No. 1; these two antidotes, together with Antidote No. 13, (except at 0.56 kg/ha of Herbicide No. 1, 4.48 kg/ha of Herbicide No. 13 and 2.24 kg/ha of antidote) provided commercial-level safening of corn, while providing excellent control of barnyardgrass and suppression-to-excellent control of velvetleaf.

EXAMPLE 11

In this example, yet another α-chloroacetanilide co-herbicide, metazachlor (Herbicide No. 14) was combined with Herbicide No. 1 for investigation of the effect of various safeners on that composition. Metazachlor is the active ingredient in the commercial herbicide BUTISAN® S, used here as a 500 g/L formulation. Again, Procedure II was followed in conducting this test, the results of which are shown in Table 11.

TABLE 11

| Herbicide Kg/ha | | Antidote Kg/ha | | % Injury | | |
|---|---|---|---|---|---|---|
| No. 1 | No. 14 | No. | Rate | Corn | BYG | VL |
| 1.12 | 3.36 | — | — | 97 | 99 | 95 |
| 0.56 | " | — | — | 93 | 99 | 85 |
| 1.12 | " | 15 | 8.96 | 40 | 100 | 85 |
| 0.56 | " | 15 | " | 65 | 100 | 90 |
| 1.12 | " | 15 | 2.24 | 25 | 100 | 85 |
| 0.56 | " | 15 | " | 65 | 100 | 90 |
| 1.12 | " | 7 | 8.96 | 45 | 99 | 90 |
| 0.56 | " | 7 | " | 45 | 100 | 85 |
| 1.12 | " | 7 | 2.24 | 70 | 99 | 90 |
| 0.56 | " | 7 | " | 10 | 99 | 80 |
| 1.12 | " | 1 | 8.96 | 50 | 100 | 80 |
| 0.56 | " | 1 | " | 50 | 100 | 90 |
| 1.12 | " | 1 | 2.24 | 45 | 99 | 85 |
| 0.56 | " | 1 | " | 25 | 99 | 80 |
| 1.12 | " | 2 | 8.96 | 75 | 100 | 85 |
| 0.56 | " | 2 | " | 75 | 99 | 90 |
| 1.12 | " | 2 | 2.24 | 75 | 100 | 97 |
| 0.56 | " | 2 | " | 75 | 99 | 85 |
| 1.12 | " | 13 | 8.96 | 70 | 100 | 95 |
| 0.56 | " | 13 | " | 40 | 100 | 85 |
| 1.12 | " | 13 | 2.24 | 60 | 100 | 90 |
| 0.56 | " | 13 | " | 75 | 100 | 85 |
| 1.12 | — | — | — | 65 | 80 | 80 |
| 0.56 | — | — | — | 65 | 75 | 75 |
| — | 3.36 | — | — | 85 | 100 | 65 |
| Control | | | | 0 | 0 | 0 |

As shown by the data in Table 11, injury to corn by Herbicides 1 and 14 both alone and in combination was excessive. Although the various antidotes effected reduced injury to corn in varying degrees (markedly so in some instances), this particular combination of herbicides at the rates tested did not experience the generally dramatic safening of other combinations of herbicides. In these tests the dichloroacetamide antidotes (Nos. 1, 7 and 15) outperformed the antidotes (2 and 13) of other chemistries.

EXAMPLE 12

This example was designed to investigate the efficacy of thirteen different antidotes from different classes of chemistry as safeners against compositions of Herbicide No. 1 and acetochlor (Herbicide No. 6) as co-herbicide. Acetochlor is the active ingredient in the commercial herbicides GUARDIAN® and WENNER®.

The test procedure used in this example was Procedure II described above. Test results are shown in Table 12.

TABLE 12

| Herbicide Kg/ha | | Antidote Kg/ha | | % Injury | | |
|---|---|---|---|---|---|---|
| No. 1 | No. 6 | No. | Rate | Corn | BYG | VL |
| 0.56 | 2.24 | — | — | 45 | 100 | 95 |
| 0.14 | " | — | — | 25 | 100 | 75 |
| 0.56 | " | 15 | 8.96 | 5 | 100 | 80 |
| 0.14 | " | 15 | " | 10 | 100 | 75 |
| 0.56 | " | 15 | 2.24 | 20 | 100 | 90 |
| 0.14 | " | 15 | " | 15 | 100 | 70 |
| 0.56 | " | 7 | 8.96 | 5 | 100 | 75 |
| 0.14 | " | 7 | " | 5 | 100 | 65 |
| 0.56 | " | 7 | 2.24 | 20 | 100 | 85 |
| 0.14 | " | 7 | " | 15 | 100 | 80 |
| 0.56 | " | 1 | 8.96 | 15 | 100 | 80 |
| 0.14 | " | 1 | " | 10 | 100 | 80 |
| 0.56 | " | 1 | 2.24 | 15 | 100 | 80 |
| 0.14 | " | 1 | " | 10 | 100 | 65 |
| 0.56 | " | 5 | 8.96 | 5 | 100 | 90 |
| 0.14 | " | 5 | " | 10 | 100 | 85 |
| 0.56 | " | 5 | 2.24 | 10 | 100 | 85 |
| 0.14 | " | 5 | " | 5 | 100 | 75 |
| 0.56 | " | 10 | 8.96 | 10 | 100 | 90 |
| 0.14 | " | 10 | " | 10 | 100 | 80 |
| 0.56 | " | 10 | 2.24 | 30 | 100 | 80 |
| 0.14 | " | 10 | " | 10 | 100 | 75 |
| 0.56 | " | 3 | 8.96 | 20 | 100 | 90 |
| 0.14 | " | 3 | " | 15 | 100 | 70 |
| 0.56 | " | 3 | 2.24 | 15 | 100 | 80 |
| 0.14 | " | 3 | " | 10 | 100 | 75 |
| 0.56 | 2.24 | 12 | 8.96 | 15 | 100 | 85 |
| 0.14 | " | 12 | " | 10 | 100 | 85 |
| 0.56 | " | 12 | 2.24 | 25 | 100 | 95 |
| 0.14 | " | 12 | " | 15 | 100 | 75 |
| 0.56 | " | 9 | 8.96 | 25 | 100 | 75 |
| 0.14 | " | 9 | " | 15 | 100 | 75 |
| 0.56 | " | 9 | 2.24 | 20 | 100 | 90 |
| 0.14 | " | 9 | " | 15 | 100 | 65 |
| 0.56 | " | 8 | 8.96 | 10 | 100 | 80 |
| 0.14 | " | 8 | " | 10 | 100 | 70 |
| 0.56 | " | 8 | 2.24 | 20 | 100 | 90 |
| 0.14 | " | 8 | " | 15 | 100 | 85 |
| 0.56 | " | 2 | 8.96 | 25 | 100 | 90 |
| 0.14 | " | 2 | " | 20 | 100 | 70 |
| 0.56 | " | 2 | 2.24 | 10 | 100 | 85 |
| 0.14 | " | 2 | " | 20 | 100 | 75 |
| 0.56 | " | 13 | 8.96 | 40 | 100 | 90 |
| 0.14 | " | 13 | " | 30 | 100 | 85 |
| 0.56 | " | 13 | 2.24 | 35 | 100 | 95 |
| 0.14 | " | 13 | " | 10 | 100 | 80 |
| 0.56 | " | 4 | 8.96 | 25 | 100 | 95 |
| 0.14 | " | 4 | " | 35 | 100 | 80 |
| 0.56 | " | 4 | 2.24 | 40 | 100 | 90 |
| 0.14 | " | 4 | " | 25 | 100 | 65 |
| 0.56 | 2.24 | 6 | 8.96 | 20 | 100 | 80 |
| 0.14 | " | 6 | " | 15 | 100 | 80 |
| 0.56 | " | 6 | 2.24 | 20 | 100 | 75 |
| 0.14 | " | 6 | " | 15 | 100 | 90 |
| 0.56 | — | — | — | 20 | 75 | 85 |
| 0.14 | — | — | — | 15 | 55 | 50 |

TABLE 12-continued

| Herbicide Kg/ha | | Antidote Kg/ha | | % Injury | | |
|---|---|---|---|---|---|---|
| No. 1 | No. 6 | No. | Rate | Corn | BYG | VL |
| — | 2.24 | — | — | 25 | 100 | 10 |
| Control | | | | 0 | 0 | 0 |

Reference to the data in Table 12 shows that without an antidote, Herbicide No. 1 at 0.56 kg/ha and Herbicide No. 6 at 2.24 kg/ha (highest test rates) caused, respectively 20% and 25% injury to corn, thus giving a combined corn injury at the same rates of 45%. However, when an antidote was added at 8.96 kg/ha, corn injury was dramatically reduced in all cases, except that of Herbicide No. 13, and most dramatically so in the case of the dichloroacetamide antidotes (Nos. 15, 7, 1, 5, 10, 3, 12, 9 and 8). At maximum test rates all dichloroacetamide antidotes, except Nos. 3 and 9, reduced corn injury to commercially-acceptable levels and when the application rate of Herbicide No. 1 was reduced to 0.14 kg/ha even Antidotes 3 and 9 reduced herbicidal injury to corn to commercial levels.

In similar, but less spectacular manner, the non-dichloroacetamide antidotes performed at commercial levels within certain combinations of herbicide(s) and antidotes as follows: Antidote No. 6 in compositions comprising Herbicide No. 1:Herbicide 6:Antidote ratios of 0.14:2.24:8.96 kg/ha; Antidote No. 2 and said herbicides:antidote ratios of 0.56:2.24:2.24 kg/ha and Antidotes 6 and 13 and said herbicides:antidote ratios of 0.14:2.24:2.24 kg/ha.

In all of the above tests, barnyardgrass control was total and that of velvetleaf generally comparable to that of the herbicide combinations without a safener.

EXAMPLE 13

In this example a plurality of dichloroacetamide antidotes were tested for their safening efficacy against a herbicidal composition comprising Herbicide No. 1 and a co-herbicide, acetochlor (Herbicide No. 6) in corn in the presence of velvetleaf. The procedure used in this example was Procedure II above. Test results are shown in Table 13.

TABLE 13

| Herbicide Kg/ha | | Antidote Kg/ha | | % Injury | |
|---|---|---|---|---|---|
| No. 1 | No. 6 | No. | Rate | Corn | VL |
| 0.14 | — | — | — | 10 | 95 |
| 0.56 | — | — | — | 55 | 85 |
| 2.24 | — | — | — | 80 | 95 |
| — | 4.48 | — | — | 50 | 10 |
| 0.56 | " | — | — | 65 | 100 |
| — | " | 1 | 0.56 | 20 | 100 |
| 0.56 | " | 1 | " | 5 | 5 |
| — | " | 1 | 2.24 | 10 | 60 |
| 0.56 | " | 1 | " | 10 | 85 |
| — | " | 3 | 0.56 | 10 | 80 |
| 0.56 | " | 3 | " | 40 | 100 |
| — | " | 3 | 2.24 | 5 | 0 |
| 0.56 | " | 3 | " | 10 | 95 |
| — | " | 5 | 0.56 | 5 | 0 |
| 0.56 | " | 5 | " | 10 | 90 |
| — | " | 5 | 2.24 | 15 | 30 |
| 0.56 | " | 5 | " | 10 | 100 |
| — | " | 7 | 0.56 | 0 | 0 |
| 0.56 | " | 7 | " | 25 | 95 |
| — | " | 7 | 2.24 | 5 | 40 |

TABLE 13-continued

| Herbicide Kg/ha | | Antidote Kg/ha | | % Injury | |
|---|---|---|---|---|---|
| No. 1 | No. 6 | No. | Rate | Corn | VL |
| 0.56 | " | 7 | " | — | — |
| — | " | 10 | 0.56 | 15 | 30 |
| 0.56 | " | 10 | " | 40 | 100 |
| — | " | 10 | 2.24 | 5 | 0 |
| 0.56 | " | 10 | " | 40 | 9 |
| — | " | 12 | 0.56 | 25 | 60 |
| 0.56 | " | 12 | " | 10 | 100 |
| — | " | 12 | 2.24 | 10 | 25 |
| 0.56 | " | 12 | " | 10 | 100 |
| — | " | 14 | 0.56 | 5 | 0 |
| 0.56 | " | 14 | " | 15 | 100 |
| — | " | 14 | 2.24 | 5 | 60 |
| 0.56 | " | 14 | " | 15 | 95 |
| — | " | 15 | 0.56 | 5 | 20 |
| 0.56 | " | 15 | " | 5 | 100 |
| — | " | 15 | 2.24 | 15 | 95 |
| 0.56 | " | 15 | " | 15 | 90 |

It will be noted that all antidotes in the test of Example 13 reduced corn injury from the herbicides used separately or in combination when applied at higher application rates. The importance of velvetleaf control by Herbicide No. 1 is apparent by reference to the low weed control values when that herbicide was omitted from the composition.

Antidote No. 15 was most active overall followed, in order, by Nos. 14, 1, 12, 7 and 10. Commercial-level safening was exhibited at all rates and combinations by Antidote Nos. 5, 14 and 15.

EXAMPLE 14

In this example, Antidote No. 17 was tested to determine its efficacy against a herbicidal combination of Herbicide No. 1 and metolachlor (Herbicide No. 12) as co-herbicide; (metolachlor is the active ingredient in DUAL® herbicide). This test was conducted under the identical test conditions described and performed in Example 13. Test results are shown in Table 14; application rate of the chemicals was in kg/ha.

TABLE 14

| Herbicide | Herbicide | Antidote | % Injury | |
|---|---|---|---|---|
| No. 1 | No. 12 | No. 17 | Corn | VL |
| 0.14 | 4.48 | 0.15 | 15 | 90 |
| 0.56 | " | " | 25 | 95 |
| 2.24 | " | " | 80 | 100 |

The above test results show that Antidote No. 17, even at the low rate of 0.15 kg/ha was able to safen corn against the combination of herbicides (No. 1:No. 12 ratio of 0.14:4.48) to commercially-acceptable levels. Such safening was reduced and largely lost at higher rates of application of Herbicide No. 1. However, that reduced safety undoubtedly would be restored by increasing the antidote concentration to a commensurate and appropriate level.

In preceding examples describing safened herbicidal compositions according to this invention, the co-herbicidal compounds were α-chloroacetamides. In Examples 15-22 below are described safened herbicidal compositions comprising combinations of a sulfonylurea compound according to Formula I (and IA) and as a co-herbicidal compound important commercial herbicides from the thiocarbamate class of chemistry.

EXAMPLE 15

This example describes experiments designed to investigate the antidotal efficacy of a plurality of antidotes against the herbicidal action of a combination of Herbicide No. 1 and butylate in corn and the prevalent weeds barnyardgrass and velvetleaf. The antidotes used in these experiments were Nos. 1-10, 12, 13 and 15.

The test procedure used in these experiments was that of Procedure II described above. The antidotes were applied to a soil cover layer by pipet after spraying the herbicides onto the soil, followed by incorporation and overhead irrigation. Test results are shown in Table 15.

TABLE 15

| Herbicide Kg/ha | | Antidote Kg/ha | | % Injury | | |
|---|---|---|---|---|---|---|
| No. 1 | No. 10 | No. | Rate | Corn | BYG | VL |
| 1.12 | 6.72 | — | — | 25 | 98 | 85 |
| 0.56 | " | — | — | 20 | 97 | 80 |
| 1.12 | " | 15 | 8.96 | 15 | 97 | 85 |
| 0.56 | " | 15 | " | 10 | 99 | 80 |
| 1.12 | " | 15 | 2.24 | 15 | 97 | 85 |
| 0.56 | " | 15 | " | 20 | 98 | 75 |
| 1.12 | " | 7 | 8.96 | 10 | 98 | 85 |
| 0.56 | " | 7 | " | 0 | 98 | 70 |
| 1.12 | " | 7 | 2.24 | 20 | 90 | 85 |
| 0.56 | " | 7 | " | 15 | 95 | 80 |
| 1.12 | " | 1 | 8.96 | 30 | 90 | 65 |
| 0.56 | " | 1 | " | 10 | 90 | 70 |
| 1.12 | " | 1 | 2.24 | 20 | 93 | 70 |
| 0.56 | " | 1 | " | 15 | 97 | 80 |
| 1.12 | " | 5 | 8.96 | 15 | 98 | 85 |
| 0.56 | " | 5 | " | 20 | 95 | 70 |
| 1.12 | " | 5 | 2.24 | 10 | 90 | 85 |
| 0.56 | " | 5 | " | 5 | 97 | 85 |
| 1.12 | " | 10 | 8.96 | 10 | 98 | 85 |
| 0.56 | " | 10 | " | 5 | 96 | 70 |
| 1.12 | " | 10 | 2.24 | 20 | 96 | 80 |
| 0.56 | " | 10 | " | 5 | 97 | 70 |
| 1.12 | " | 3 | 8.96 | 15 | 97 | 80 |
| 0.56 | " | 3 | " | 10 | 97 | 80 |
| 1.12 | " | 3 | 2.24 | 5 | 93 | 80 |
| 0.56 | " | 3 | " | 15 | 95 | 75 |
| 1.12 | 6.72 | 12 | 8.96 | 20 | 98 | 80 |
| 0.56 | " | 12 | " | 0 | 96 | 80 |
| 1.12 | " | 12 | 2.24 | 35 | 97 | 85 |
| 0.56 | " | 12 | " | 10 | 90 | 75 |
| 1.12 | " | 9 | 8.96 | 15 | 97 | 80 |
| 0.56 | " | 9 | " | 15 | 95 | 70 |
| 1.12 | " | 9 | 2.24 | 5 | 97 | 80 |
| 0.56 | " | 9 | " | 15 | 97 | 65 |
| 1.12 | " | 8 | 8.96 | 20 | 85 | 85 |
| 0.56 | " | 8 | " | 10 | 90 | 70 |
| 1.12 | " | 8 | 2.24 | 5 | 95 | 80 |
| 0.56 | " | 8 | " | 0 | 93 | 75 |
| 1.12 | " | 2 | 8.96 | 20 | 98 | 85 |
| 0.56 | " | 2 | " | 15 | 90 | 75 |
| 1.12 | " | 2 | 2.24 | 10 | 96 | 85 |
| 0.56 | " | 2 | " | 25 | 96 | 75 |
| 1.12 | " | 13 | 8.96 | 0 | 95 | 85 |
| 0.56 | " | 13 | " | 15 | 95 | 70 |
| 1.12 | " | 13 | 2.24 | 20 | 97 | 90 |
| 0.56 | " | 13 | " | 10 | 97 | 85 |
| 1.12 | " | 4 | 8.96 | 25 | 90 | 85 |
| 0.56 | " | 4 | " | 5 | 85 | 85 |
| 1.12 | " | 4 | 2.24 | 15 | 95 | 85 |
| 0.56 | " | 4 | " | 15 | 93 | 85 |
| 1.12 | 6.72 | 6 | 8.96 | 20 | 99 | 95 |
| 0.56 | " | 6 | " | 20 | 97 | 85 |
| 1.12 | " | 6 | 2.24 | 10 | 98 | 90 |
| 0.56 | " | 6 | " | 5 | 95 | 80 |
| 1.12 | — | — | — | 20 | 55 | 70 |
| 0.56 | — | — | — | 20 | 35 | 50 |
| — | 6.72 | — | — | 5 | 97 | 55 |
| Control | | | | 0 | 0 | 0 |

Referring to the data in Table 15, it is noted that all of the antidotes tested against Herbicide No. 1 at the 1.12 and 0.56 kg/ha rates combined with Herbicide No. 10 at 6.72 kg/ha PPI (preplant incorporated) reduced injury to the corn at one or both rates to commercially-acceptable levels. In this test, the best safening effect at the highest rate was achieved by Antidote No. 13 closely followed by Antidote Nos. 7 and 10. At various combinations of rates of the two herbicides and antidotes, four antidotes (Nos. 7, 8, 12 and 13) provided complete protection against corn injury while maintaining excellent control of barnyardgrass and good control or suppression of velvetleaf.

EXAMPLE 16

In this example, the same antidotes and procedure as described in the preceding example were used, except that the co-herbicide in the experiments of this example was EPTC, active ingredient in the commercial herbicide EPTAM®; EPTC is identified as Herbicide No. 4.

Test results are shown in Table 16.

TABLE 16

| Herbicide Kg/ha | | Antidote Kg/ha | | % Injury | | |
|---|---|---|---|---|---|---|
| No. 1 | EPTAM | No. | Rate | Corn | BYG | VL |
| 1.12 | 6.72 | — | — | 25 | 90 | 85 |
| 0.56 | " | — | — | 25 | 93 | 80 |
| 1.12 | " | 15 | 8.96 | 15 | 85 | 75 |
| 0.56 | " | 15 | " | 10 | 85 | 75 |
| 1.12 | " | 15 | 2.24 | 5 | 80 | 70 |
| 0.56 | " | 15 | " | 10 | 85 | 75 |
| 1.12 | " | 7 | 8.96 | 20 | 75 | 80 |
| 0.56 | " | 7 | " | 5 | 80 | 75 |
| 1.12 | " | 7 | 2.24 | 5 | 75 | 80 |
| 0.56 | " | 7 | " | 0 | 80 | 80 |
| 1.12 | " | 1 | 8.96 | 15 | 85 | 75 |
| 0.56 | " | 1 | " | 0 | 95 | 70 |
| 1.12 | " | 1 | 2.24 | 0 | 85 | 80 |
| 0.56 | " | 1 | " | 0 | 80 | 80 |
| 1.12 | " | 5 | 8.96 | 10 | 75 | 85 |
| 0.56 | " | 5 | " | 15 | 80 | 80 |
| 1.12 | " | 5 | 2.24 | 10 | 80 | 85 |
| 0.56 | " | 5 | " | 0 | 80 | 80 |
| 1.12 | " | 10 | 8.96 | 5 | 95 | 85 |
| 0.56 | " | 10 | " | 5 | 98 | 80 |
| 1.12 | " | 10 | 2.24 | 20 | 85 | 85 |
| 0.56 | " | 10 | " | 0 | 85 | 85 |
| 1.12 | " | 3 | 8.96 | 15 | 85 | 80 |
| 0.56 | " | 3 | " | 15 | 85 | 80 |
| 1.12 | " | 3 | 2.24 | 0 | 85 | 80 |
| 0.56 | " | 3 | " | 15 | 85 | 85 |
| 1.12 | 6.72 | 12 | 8.96 | 10 | 90 | 85 |
| 0.56 | " | 12 | " | 15 | 85 | 75 |
| 1.12 | " | 12 | 2.24 | 0 | 90 | 85 |
| 0.56 | " | 12 | " | 5 | 90 | 85 |
| 1.12 | " | 9 | 8.96 | 15 | 75 | 75 |
| 0.56 | " | 9 | " | 10 | 80 | 75 |
| 1.12 | " | 9 | 2.24 | 0 | 80 | 80 |
| 0.56 | " | 9 | " | 5 | 85 | 85 |
| 1.12 | " | 8 | 8.96 | 25 | 75 | 80 |
| 0.56 | " | 8 | " | 10 | 85 | 80 |
| 1.12 | " | 8 | 2.24 | 25 | 80 | 80 |
| 0.56 | " | 8 | " | 5 | 80 | 80 |
| 1.12 | " | 2 | 8.96 | 5 | 85 | 85 |
| 0.56 | " | 2 | " | 0 | 80 | 80 |
| 1.12 | " | 2 | 2.24 | 15 | 90 | 80 |
| 0.56 | " | 2 | " | 5 | 85 | 75 |
| 1.12 | " | 13 | 8.96 | 10 | 75 | 80 |
| 0.56 | " | 13 | " | 0 | 80 | 75 |
| 1.12 | " | 13 | 2.24 | 15 | 85 | 85 |
| 0.56 | " | 13 | " | 10 | 85 | 85 |
| 1.12 | " | 4 | 8.96 | 5 | 85 | 80 |
| 0.56 | " | 4 | " | 0 | 90 | 80 |

TABLE 16-continued

| Herbicide Kg/ha | | Antidote Kg/ha | | % Injury | | |
|---|---|---|---|---|---|---|
| No. 1 | EPTAM | No. | Rate | Corn | BYG | VL |
| 1.12 | " | 4 | 2.24 | 30 | 80 | 80 |
| 0.56 | " | 4 | " | 10 | 80 | 80 |
| 1.12 | " | 6 | 8.96 | 10 | 90 | 90 |
| 0.56 | " | 6 | " | 0 | 90 | 85 |
| 1.12 | " | 6 | 2.24 | 5 | 85 | 85 |
| 0.56 | " | 6 | " | 15 | 85 | 80 |
| 0.56 | — | — | — | 10 | 70 | 60 |
| 1.12 | — | — | — | 15 | 55 | 40 |
| — | 6.72 | — | — | 5 | 95 | 55 |
| Control | | | | 0 | 0 | 0 |

The data in Table 16 show that for the combination of the highest test rates of Herbicide No. 1 at 1.12 kg/ha plus EPTAM at 6.72 kg/ha), all of the antidotes, except No. 8, safened corn. In addition, herbicidal injury to corn by all other combinations of Herbicides No. 1 and EPTAM was reduced, except for that of Antidote No. 4 for the combination of Herbicide No. 1 at 1.12 kg/ha, EPTAM at 6.72 kg/ha and the antidote at 2.24 kg/ha. Seven dichloroacetamide antidotes and Herbicides 1, 4, 6 and 13 from other chemistries demonstrated commercial control of barnyardgrass and control or suppression of the velvetleaf.

EXAMPLE 17

In this example, the co-herbicidal compound tested in the composition with Herbicide No. 1 was vernolate (Herbicide No. 11); this compound is the active ingredient in VERNAM® herbicide. The antidotes and procedure used in these experiments were the same as in Examples 15 and 16. Test results are shown in Table 17.

TABLE 17

| Herbicide Kg/ha | | Antidote Kg/ha | | % Injury | | |
|---|---|---|---|---|---|---|
| No. 1 | VERNAM | No. | Rate | Corn | BYG | VL |
| 1.12 | 6.72 | — | — | 70 | 99 | 85 |
| 0.56 | " | — | — | 75 | 99 | 85 |
| 1.12 | " | 15 | 8.96 | 0 | 99 | 95 |
| 0.56 | " | 15 | " | 15 | 99 | 80 |
| 1.12 | " | 15 | 2.24 | 15 | 99 | 80 |
| 0.56 | " | 15 | " | 0 | 99 | 85 |
| 1.12 | " | 7 | 8.96 | 5 | 99 | 98 |
| 0.56 | " | 7 | 11 | 10 | 99 | 95 |
| 1.12 | " | 7 | 2.24 | 15 | 99 | 85 |
| 0.56 | " | 7 | " | 0 | 99 | 90 |
| 1.12 | " | 1 | 8.96 | 10 | 99 | 85 |
| 0.56 | " | 1 | " | 0 | 98 | 80 |
| 1.12 | " | 1 | 2.24 | 10 | 100 | 85 |
| 0.56 | " | 1 | " | 5 | 98 | 85 |
| 1.12 | " | 5 | 8.96 | 5 | 98 | 97 |
| 0.56 | " | 5 | " | 10 | 99 | 90 |
| 1.12 | " | 5 | 2.24 | 10 | 99 | 85 |
| 0.56 | " | 5 | " | 15 | 99 | 85 |
| 1.12 | " | 10 | 8.96 | 15 | 99 | 95 |
| 0.56 | " | 10 | " | 10 | 99 | 90 |
| 1.12 | " | 10 | 2.24 | 10 | 99 | 90 |
| 0.56 | " | 10 | " | 5 | 99 | 95 |
| 1.12 | " | 3 | 8.96 | 0 | 99 | 85 |
| 0.56 | " | 3 | " | 15 | 99 | 90 |
| 1.12 | " | 3 | 2.24 | 10 | 99 | 90 |
| 0.56 | " | 3 | " | 15 | 99 | 85 |
| 1.12 | 6.72 | 12 | 8.96 | 5 | 99 | 85 |
| 0.56 | " | 12 | " | 10 | 99 | 85 |
| 1.12 | " | 12 | 2.24 | 15 | 99 | 90 |
| 0.56 | " | 12 | " | 5 | 99 | 85 |
| 1.12 | " | 9 | 8.96 | 0 | 99 | 95 |

TABLE 17-continued

| Herbicide Kg/ha | | Antidote Kg/ha | | % Injury | | |
|---|---|---|---|---|---|---|
| No. 1 | VERNAM | No. | Rate | Corn | BYG | VL |
| 0.56 | " | 9 | " | 5 | 99 | 85 |
| 1.12 | " | 9 | 2.24 | 10 | 99 | 85 |
| 0.56 | " | 9 | " | 5 | 99 | 90 |
| 1.12 | " | 8 | 8.96 | 10 | 99 | 85 |
| 0.56 | " | 8 | " | 0 | 99 | 90 |
| 1.12 | " | 8 | 2.24 | 15 | 99 | 95 |
| 0.56 | " | 8 | " | 15 | 99 | 95 |
| 1.12 | " | 2 | 8.96 | 15 | 99 | 80 |
| 0.56 | " | 2 | " | 25 | 99 | 80 |
| 1.12 | " | 2 | 2.24 | 25 | 98 | 85 |
| 0.56 | " | 2 | " | 35 | 98 | 85 |
| 1.12 | " | 13 | 8.96 | 10 | 99 | 85 |
| 0.56 | " | 13 | " | 25 | 99 | 85 |
| 1.12 | " | 13 | 2.24 | 15 | 99 | 85 |
| 0.56 | " | 13 | " | 15 | 99 | 85 |
| 1.12 | " | 4 | 8.96 | 20 | 99 | 85 |
| 0.56 | " | 4 | " | 15 | 99 | 90 |
| 1.12 | " | 4 | 2.24 | 25 | 99 | 85 |
| 0.56 | " | 4 | " | 15 | 99 | 80 |
| 1.12 | " | 6 | 8.96 | 15 | 100 | 95 |
| 0.56 | " | 6 | " | 20 | 99 | 90 |
| 1.12 | " | 6 | 2.24 | 35 | 99 | 95 |
| 0.56 | " | 6 | " | 25 | 99 | 80 |
| 1.12 | — | — | — | 5 | 45 | 65 |
| 0.56 | — | — | — | 0 | 25 | 10 |
| — | 6.72 | — | — | 80 | 100 | 75 |
| Control | | | | 0 | 0 | 0 |

The data in Table 17 show that at one or more combinations of rates of herbicides and antidotes, all antidotes exhibited commercial-level safening of the herbicidal combination of the sulfonylurea Herbicide No. 1 and the thiocarbamate, vernolate, without lessening the excellent barnyardgrass and good-to-excellent velvetleaf weed control. In fact, all antidotes, except Nos. 2, 4, 6 and 13, safened all combinations of the two herbicides to commercial-level safety. Again, the dichloroacetamide antidotes were more effective to minimize corn damage (mainly caused by the vernolate) than other types of antidotes. In this test, the best overall safening performance was achieved by Antidote No. 9.

EXAMPLE 18

In the test reported in this example, the herbicidal composition was similar to that used in Example 16 in that Herbicide No. 1 was combined with EPTC (Herbicide No. 4) as a co-herbicide and the antidotes included Nos. 1, 2, 7, 13 and 15. However, in this test the EPTC was introduced as a formulation of ERADICANE (EPTC+the antidote R-25788, i.e., Antidote No. 1) at an application rate of 8.96 kg/ha. Thus, in this test two antidotes were present, viz. R-25788 and one of the auxilliary antidotes, No. 2, 13 and 15.

Test procedures were those of Procedure II above. Test results are shown in Table 18.

TABLE 18

| Herbicide Kg/ha | | Antidote Kg/ha | | % Injury | | |
|---|---|---|---|---|---|---|
| No. 1 | ERADICANE | No. | Rate | Corn | BYG | VL |
| 1.12 | 8.96 | — | — | 20 | 85 | 75 |
| 0.56 | " | — | — | 25 | 90 | 80 |
| 0.56 | " | 15 | 8.96 | 25 | 90 | 85 |
| 1.12 | " | 15 | " | 30 | 85 | 65 |

TABLE 18-continued

| Herbicide Kg/ha | | Antidote Kg/ha | | % Injury | | |
|---|---|---|---|---|---|---|
| No. 1 | ERADICANE | No. | Rate | Corn | BYG | VL |
| 0.56 | " | 15 | 2.24 | 25 | 90 | 80 |
| 1.12 | " | 15 | " | 15 | 93 | 80 |
| 0.56 | " | 7 | 8.96 | 20 | 85 | 80 |
| 1.12 | " | 7 | " | 10 | 85 | 75 |
| 0.56 | " | 7 | 2.24 | 15 | 90 | 75 |
| 1.12 | " | 7 | " | 15 | 85 | 70 |
| 0.56 | " | 1 | 8.96 | 25 | 90 | 85 |
| 1.12 | " | 1 | " | 25 | 85 | 75 |
| 0.56 | " | 1 | 2.24 | 30 | 90 | 85 |
| 1.12 | " | 1 | " | 35 | 90 | 75 |
| 0.56 | " | 2 | 8.96 | 25 | 85 | 93 |
| 1.12 | " | 2 | " | 20 | 95 | 75 |
| 0.56 | " | 2 | 2.24 | 15 | 93 | 80 |
| 1.12 | " | 2 | " | 20 | 85 | 70 |
| 0.56 | " | 13 | 8.96 | 20 | 85 | 80 |
| 1.12 | " | 13 | " | 40 | 90 | 75 |
| 0.56 | " | 13 | 2.24 | 10 | 85 | 80 |
| 1.12 | " | 13 | " | 10 | 85 | 75 |
| 1.12 | — | — | — | 25 | 55 | 55 |
| 0.56 | — | — | — | 30 | 30 | 45 |
| — | 8.96 | — | — | 10 | 95 | 35 |
| Control | | | | 0 | 0 | 0 |

In this test in Table 18 in the PPI mode of application of chemicals, control of barnyardgrass and suppression of velvetleaf occurred, but with marginal corn safety. Although corn injury across four treatments was slightly lower with Antidote No. 7, other safeners did not lessen this marginal level corn injury at the highest test rates of the herbicides and safeners.

EXAMPLE 19

The test reported in this example was performed in the same manner and with the same antidotes used in Example 18, the only difference being the substitution of the commercial herbicidal product ERADICANE® EXTRA for ERADICANE®. ERADICANE EXTRA is a formulation containing both an antidote, i.e., R-29148 (Antidote No. 5 herein), and an extender, dietholate.

Test results are set forth in Table 19.

TABLE 19

| Herbicide Kg/ha | | Antidote Kg/ha | | % Injury | | |
|---|---|---|---|---|---|---|
| No. 1 | ERADICANE EXTRA | No. | Rate | Corn | BYG | VL |
| 1.12 | 8.96 | — | — | 20 | 95 | 85 |
| 0.56 | " | — | — | 30 | 95 | 80 |
| 1.12 | " | 15 | 8.96 | 25 | 90 | 75 |
| 0.56 | " | 15 | " | 30 | 85 | 75 |
| 1.12 | " | 15 | 2.24 | 25 | 85 | 85 |
| 0.56 | " | 15 | " | 20 | 90 | 70 |
| 1.12 | " | 7 | 8.96 | 25 | 85 | 85 |
| 0.56 | " | 7 | " | 20 | 85 | 80 |
| 1.12 | " | 7 | 2.24 | 25 | 90 | 75 |
| 0.56 | " | 7 | " | 15 | 85 | 75 |
| 1.12 | " | 1 | 8.96 | 25 | 95 | 85 |
| 0.56 | " | 1 | " | 15 | 90 | 75 |
| 1.12 | " | 1 | 2.24 | 35 | 90 | 70 |
| 0.56 | " | 1 | " | 35 | 90 | 70 |
| 1.12 | " | 2 | 8.96 | 20 | 85 | 75 |
| 0.56 | " | 2 | " | 25 | 90 | 75 |
| 1.12 | " | 2 | 2.24 | 25 | 85 | 85 |
| 0.56 | " | 2 | " | 20 | 90 | 75 |

TABLE 19-continued

| Herbicide Kg/ha | | Antidote Kg/ha | | % Injury | | |
|---|---|---|---|---|---|---|
| No. 1 | ERADICANE EXTRA | No. | Rate | Corn | BYG | VL |
| 1.12 | " | 13 | 8.96 | 15 | 95 | 85 |
| 0.56 | " | 13 | " | 15 | 90 | 70 |
| 1.12 | " | 13 | 2.24 | 20 | 90 | 80 |
| 0.56 | " | 13 | " | 25 | 90 | 65 |
| 1.12 | — | — | — | 25 | 70 | 65 |
| 0.56 | — | — | — | 20 | 30 | 50 |
| — | 8.96 | — | — | 5 | 98 | 55 |
| Control | | | | 0 | 0 | 0 |

The addition of other antidotes to the EPTC formulation already containing the R-29148 antidote did in some instances reduce higher corn injury. Antidote No. 13 was the most efficacious antidote across all four treatments. On the other hand, at some combinations of rates of the herbicides and antidotes, some of the antidotes appeared to enhance corn injury in this test; e.g., at the highest rates of antidotes and herbicides, Antidote Nos. 1, 7 and 15 slightly increased corn injury from 20% to 25%. In this test good barnyardgrass control was achieved together with suppression-to-good velvetleaf control.

EXAMPLE 20

This example describes experiments designed to test two generally efficacious antidotal compounds, i.e., Antidote Nos. 5 and 15, against the herbicidal action of the sulfonylurea compound, Herbicide No. 1, and the commercial herbicides EPTC (Herbicide No. 4) and ERADICANE® EXTRA (EPTC +R-29148, Antidote No. 5). Procedure II above was used in conducting these experiments. Formulations of EPTC and ERADICANE EXTRA were applied onto soil cover layers (to be applied over seed beds), followed by sequential pipetting of Herbicide No. 1 and Antidote No. 15. The soil was mixed to homogeneity and spread over the seed beds followed by 0.6 cm of overhead irrigation. Particular interest was also concerned with velvetleaf control, hence barnyard-grass was not included in this test.

Test results are shown in Table 20.

TABLE 20

| Herbicides Kg/ha | | ERADICANE | Antidote | % Injury | |
|---|---|---|---|---|---|
| No. 1 | No. 4 | EXTRA | No. 15 | Corn | VL |
| — | — | 2.24 | — | 0 | 0 |
| — | — | 4.48 | — | 0 | 15 |
| — | — | 6.72 | — | 0 | 85 |
| — | — | — | — | 0 | 0 |
| — | 2.24 | — | — | 0 | 0 |
| — | 4.48 | — | — | 0 | 0 |
| — | 6.72 | — | — | 10 | 18 |
| 0.56 | — | — | — | 70 | 95 |
| 2.24 | — | 2.24 | — | 90 | 100 |
| 0.56 | — | " | — | 55 | 95 |
| 2.24 | — | 4.48 | — | 85 | 100 |
| 0.56 | — | " | — | 65 | 90 |
| 2.24 | — | 6.72 | — | 95 | 95 |
| 0.56 | — | " | — | 75 | 100 |
| 2.24 | — | — | — | 85 | 100 |
| 0.56 | 2.24 | — | — | 75 | 95 |
| 2.24 | " | — | — | 90 | 95 |
| 0.56 | 4.48 | — | — | 35 | 90 |

TABLE 20-continued

| Herbicides Kg/ha | | ERADICANE EXTRA | Antidote No. 15 | % Injury | |
|---|---|---|---|---|---|
| No. 1 | No. 4 | | | Corn | VL |
| 2.24 | " | — | — | 70 | 95 |
| 0.56 | 6.72 | — | — | 85 | 100 |
| 2.24 | " | — | — | 90 | 100 |
| 0.56 | 2.24 | — | 0.18 | 5 | 90 |
| 2.24 | " | — | " | 35 | 95 |
| 0.56 | 4.48 | — | 0.35 | 15 | 95 |
| 2.24 | " | — | " | 15 | 95 |
| 0.56 | 6.78 | — | 0.56 | 0 | 95 |
| 2.24 | " | — | " | 15 | 100 |

The data in Table 20 indicates that the antidote in ERADI-CANE EXTRA was not efficacious against the herbicidal combination of Herbicides No. 1 and No. 4. This result is consonant with the results in Example 18. However, these results should also be compared with those in Example 16 wherein the herbicidal combination of Herbicides No. 1 and No. 4 (not present as a formulation of ERADICANE EXTRA) was efficaciously safened by the antidote component (R-29148) in ERADICANE EXTRA, as well as a plurality of other antidotes including Antidote No. 1 (the antidote in ERADICANE), which was also shown by the test data in Table 16 to adequately safen Herbicide No. 4.

EXAMPLE 21

In this example, tests were conducted as in the preceding Examples 18-20, except here the co-herbicidal component was SUTAN® PLUS, a commercial product comprising as the active herbicidal ingredient the compound butylate (Herbicide No. 10) and an antidote R-27588 (Antidote No. 1). Again, the antidotal compounds herein were Nos. 1, 2, 7, 13 and 15. Procedure II was used. Test results are shown in Table 21.

TABLE 21

| Herbicide Kg/ha | | Antidote Kg/ha | | % Injury | | |
|---|---|---|---|---|---|---|
| No. 1 | SUTAN + | No. | Rate | Corn | BYG | VL |
| 1.12 | 8.96 | — | — | 5 | 50 | 70 |
| 0.56 | " | — | — | 10 | 20 | 60 |
| 1.12 | " | 15 | 8.96 | 20 | 40 | 65 |
| 0.56 | " | 15 | " | 25 | 10 | 60 |
| 1.12 | " | 15 | 2.24 | 30 | 15 | 65 |
| 0.56 | " | 15 | " | 25 | 0 | 50 |
| 1.12 | " | 7 | 8.96 | 15 | 10 | 45 |
| 0.56 | " | 7 | " | 20 | 10 | 65 |
| 1.12 | " | 7 | 2.24 | 15 | 40 | 65 |
| 0.56 | " | 7 | " | 5 | 25 | 45 |
| 1.12 | " | 1 | 8.96 | 20 | 35 | 60 |
| 0.56 | " | 1 | " | 15 | 25 | 65 |
| 1.12 | " | 1 | 2.24 | 30 | 10 | 65 |
| 0.56 | " | 1 | " | 15 | 0 | 40 |
| 1.12 | " | 2 | 8.96 | 15 | 5 | 70 |
| 0.56 | " | 2 | " | 5 | 10 | 65 |
| 1.12 | " | 2 | 2.24 | 0 | 45 | 70 |
| 0.56 | " | 2 | " | 10 | 5 | 55 |
| 1.12 | " | 13 | 8.96 | 10 | 70 | 70 |
| 0.56 | " | 13 | " | 10 | 50 | 40 |
| 1.12 | " | 13 | 2.24 | 5 | 70 | 70 |
| 0.56 | " | 13 | " | 0 | 40 | 55 |
| 1.12 | — | — | — | 30 | 10 | 65 |
| 0.56 | — | — | — | 0 | 10 | 50 |
| — | 8.96 | — | — | 15 | 10 | 0 |
| Control | | | | 0 | 0 | 0 |

As noted from the data in Table 21, the mixture applied PPI provided excellent corn safety. The addition of other dichloroacetamide antidotes did not improve corn safety. Although corn safety was acceptable to marginal, weed control was poor to moderate.

EXAMPLE 22

The experiments in this example were designed as a retest of those described in Example 21 in view of the uncharacteristically poor corn safety and weed control, believed to have resulted from unseasonably high temperatures in the greenhouse. Accordingly, temperatures were reduced for these tests. Test results are shown in Table 22.

TABLE 22

| Herbicide Kg/ha | | Antidote Kg/ha | | % Injury | | |
|---|---|---|---|---|---|---|
| No. 1 | SUTAN + | No. | Rate | Corn | BYG | VL |
| 1.12 | 8.96 | — | — | 60 | 93 | 85 |
| 0.56 | " | — | — | 55 | 93 | 80 |
| 1.12 | " | 15 | 8.96 | 45 | 90 | 80 |
| 0.56 | " | 15 | " | 55 | 90 | 98 |
| 1.12 | " | 15 | 2.24 | 60 | 85 | 80 |
| 0.56 | " | 15 | " | 45 | 85 | 70 |
| 1.12 | " | 7 | 8.96 | 50 | 80 | 70 |
| 0.56 | " | 7 | " | 50 | 90 | 75 |
| 1.12 | " | 7 | 2.24 | 65 | 95 | 97 |
| 0.56 | " | 7 | " | 45 | 90 | 80 |
| 1.12 | " | 1 | 8.96 | 55 | 90 | 80 |
| 0.56 | " | 1 | " | 60 | 90 | 80 |
| 1.12 | " | 1 | 2.24 | 50 | 85 | 80 |
| 0.56 | " | 1 | " | 45 | 93 | 80 |
| 1.12 | " | 2 | 8.96 | 50 | 90 | 90 |
| 0.56 | " | 2 | " | 55 | 90 | 90 |
| 1.12 | " | 2 | 2.24 | 40 | 85 | 93 |
| 0.56 | " | 2 | " | 45 | 80 | 80 |
| 1.12 | " | 13 | 8.96 | 60 | 93 | 90 |
| 0.56 | " | 13 | " | 60 | 90 | 95 |
| 1.12 | " | 13 | 2.24 | 75 | 95 | 95 |
| 0.56 | " | 13 | " | 70 | 90 | 85 |
| 1.12 | — | — | — | 65 | 70 | 80 |
| 0.56 | — | — | — | 60 | 55 | 65 |
| — | 8.96 | — | — | 5 | 100 | 75 |
| Control | | | | 0 | 0 | 0 |

As appears from the data in Table 22, all safened herbicidal compositions demonstrated excellent-to-good control of the barnyardgrass and excellent-to-moderate velvetleaf control. Moderate root pruning was noted in the corn plants. In these tests, the antidotes did not provide adequate protection against the noted root pruning, which was induced by Herbicide No. 1.

EXAMPLE 23

In other greenhouse tests, using Procedure II described above, the safening efficacy of Antidote Nos. 15 and 17–21 was evaluated against Herbicide No. 1 in corn in the presence of Giant foxtail (*Setaria fabergi*) and Velvetleaf (*Abutilon theophrasti*) as representative annual monocotyledonous and dicotyledonous weeds, respectively.

Test results are shown in Tables 23A and 23B wherein the indicated plant inhibition represents the average of duplicate replications, with observations being made thirteen (13) days after application of the chemicals. Giant foxtail and Velvetleaf are represented by the symbols "GFT" and "VL", respectively. The data in Table 23A show the test results using the antidotes at 2.24 kg/ha, whereas in Table 23B, the antidotal rate was reduced to 0.56 kg/ha.

TABLE 23A

| Herb. No. 1 Kg/Ha | Antidote No. | Antidote Kg/ha | % Inhibition Corn | % Inhibition GFT | % Inhibition VL |
|---|---|---|---|---|---|
| 1.12 | — | — | 65 | 80 | 95 |
| 0.56 | — | — | 50 | 60 | 95 |
| 0.28 | — | — | 25 | 35 | 90 |
| 0.14 | — | — | 15 | 25 | 90 |
| 1.12 | 18 | 2.24 | 10 | 70 | 95 |
| 0.56 | 18 | 2.24 | 10 | 65 | 95 |
| 0.28 | 18 | 2.24 | 0 | 30 | 95 |
| 0.14 | 18 | 2.24 | 0 | 15 | 90 |
| 1.12 | 19 | 2.24 | 15 | 70 | 95 |
| 0.56 | 19 | 2.24 | 5 | 50 | 95 |
| 0.28 | 19 | 2.24 | 0 | 30 | 85 |
| 0.14 | 19 | 2.24 | 0 | 15 | 90 |
| 1.12 | 20 | 2.24 | 15 | 65 | 90 |
| 0.56 | 20 | 2.24 | 0 | 40 | 85 |
| 0.28 | 20 | 2.24 | 0 | 35 | 90 |
| 0.14 | 20 | 2.24 | 0 | 15 | 90 |
| 1.12 | 21 | 2.24 | 30 | 70 | 95 |
| 0.56 | 21 | 2.24 | 5 | 35 | 95 |
| 0.28 | 21 | 2.24 | 0 | 20 | 85 |
| 0.14 | 21 | 2.24 | 0 | 10 | 85 |
| 1.12 | 15 | 2.24 | 20 | 75 | 98 |
| 0.56 | 15 | 2.24 | 5 | 65 | 90 |
| 0.28 | 15 | 2.24 | 0 | 30 | 90 |
| 0.14 | 15 | 2.24 | 5 | 20 | 90 |
| 1.12 | 17 | 2.24 | 25 | 70 | 95 |
| 0.56 | 17 | 2.24 | 15 | 60 | 95 |
| 0.28 | 17 | 2.24 | 0 | 25 | 85 |
| 0.14 | 17 | 2.24 | 0 | 25 | 95 |

TABLE 23B

| Herb. No. 1 Kg/Ha | Antidote No. | Antidote Kg/ha | % Inhibition Corn | % Inhibition GFT | % Inhibition VL |
|---|---|---|---|---|---|
| 1.12 | — | — | 60 | 70 | 90 |
| 0.56 | — | — | 40 | 60 | 90 |
| 0.28 | — | — | 25 | 30 | 95 |
| 0.14 | — | — | 10 | 30 | 85 |
| 1.12 | 18 | 0.56 | 30 | 60 | 95 |
| 0.56 | 18 | 0.56 | 20 | 60 | 90 |
| 0.28 | 18 | 0.56 | 5 | 20 | 95 |
| 0.14 | 18 | 0.56 | 5 | 15 | 90 |
| 1.12 | 19 | 0.56 | 40 | 65 | 90 |
| 0.56 | 19 | 0.56 | 15 | 60 | 90 |
| 0.28 | 19 | 0.56 | 5 | 40 | 85 |
| 0.14 | 19 | 0.56 | 0 | 25 | 85 |
| 1.12 | 20 | 0.56 | 40 | 75 | 95 |
| 0.56 | 20 | 0.56 | 20 | 60 | 90 |
| 0.28 | 20 | 0.56 | 5 | 20 | 90 |
| 0.14 | 20 | 0.56 | 0 | 15 | 90 |
| 1.12 | 21 | 0.56 | 35 | 75 | 95 |
| 0.56 | 21 | 0.56 | 20 | 50 | 90 |
| 0.28 | 21 | 0.56 | 5 | 45 | 90 |
| 0.14 | 21 | 0.56 | 0 | 20 | 85 |
| 1.12 | 15 | 0.56 | 10 | 70 | 95 |
| 0.56 | 15 | 0.56 | 5 | 60 | 95 |
| 0.28 | 15 | 0.56 | 0 | 30 | 90 |
| 0.14 | 15 | 0.56 | 0 | 20 | 85 |
| 1.12 | 17 | 0.56 | 30 | 65 | 95 |
| 0.56 | 17 | 0.56 | 20 | 55 | 90 |
| 0.28 | 17 | 0.56 | 10 | 40 | 90 |
| 0.14 | 17 | 0.56 | 0 | 15 | 90 |

Referring to the data in Tables 23A and 23B, it will be noted that herbicide injury due to Herbicide No. 1 with no antidote present was reduced by each of the test antidotes at appropriate herbicide:antidote ratios at both rates of application of the antidote. In particular, at 2.24 kg/ha of antidote, corn injury by Herbicide No. 1 was reduced to commercially acceptable levels (i.e., ≧15% inhibition) in all instances except with Antidote Nos. 15 and 17 at the highest herbicide test rate of 1.12 kg/ha, but at lower rates, corn safety was achieved.

Similarly, even at the lower antidote application rate of 0.56 kg/ha and herbicide rates of less than 0.28 kg/ha, commercially-acceptable corn safety was assured in all cases. Antidote No. 15 greatly safened corn against the herbicide at all test rates, while the remaining antidotes reduced corn injury by between 20% and 505 at the three highest herbicide application rates.

The test data further show that in essentially all instances, weed control was unaffected by addition of an antidote compared to weed control by the herbicide with no antidote present.

EXAMPLE 24

The tests described in Example 23 were duplicated, but in this example a variety of co-herbicides were included to ascertain the efficacy of the antidotes against combinations of Herbicide No. 1 and Herbicides Nos. 4, 6, 7 and 12 as co-herbicides. Test results are shown in Table 24, wherein the antidote application rate was 2.24 kg/ha.

TABLE 24

| Herb. No. 1 Kg/ha | Co-Herb. No. | Co-Herb. Kg/ha | Antidote No. | Antidote Kg/ha | % Inhibition Corn | % Inhibition GFT | % Inhibition VL |
|---|---|---|---|---|---|---|---|
| 0.56 | 7 | 0.28 | — | — | 45 | 99 | 95 |
| 0.28 | 7 | 0.28 | — | — | 30 | 100 | 95 |
| 0.14 | 7 | 0.28 | — | — | 15 | 100 | 90 |
| 0.07 | 7 | 0.28 | — | — | 5 | 100 | 90 |
| 0.56 | 7 | 0.28 | 18 | 2.24 | 10 | 100 | 98 |
| 0.28 | 7 | 0.28 | 18 | 2.24 | 5 | 100 | 95 |
| 0.14 | 7 | 0.28 | 18 | 2.24 | 10 | 99 | 95 |
| 0.07 | 7 | 0.28 | 18 | 2.24 | 0 | 99 | 90 |
| 0.56 | 7 | 0.28 | 19 | 2.24 | 10 | 99 | 98 |
| 0.28 | 7 | 0.28 | 19 | 2.24 | 5 | 99 | 95 |
| 0.14 | 7 | 0.28 | 19 | 2.24 | 0 | 99 | 90 |
| 0.07 | 7 | 0.28 | 19 | 2.24 | 0 | 99 | 90 |
| 0.56 | 7 | 0.28 | 20 | 2.24 | 5 | 99 | 95 |
| 0.28 | 7 | 0.28 | 20 | 2.24 | 0 | 100 | 95 |
| 0.14 | 7 | 0.28 | 20 | 2.24 | 0 | 98 | 90 |
| 0.07 | 7 | 0.28 | 20 | 2.24 | 0 | 98 | 95 |
| 0.56 | 7 | 0.28 | 21 | 2.24 | 15 | 100 | 98 |
| 0.28 | 7 | 0.28 | 21 | 2.24 | 5 | 98 | 95 |
| 0.14 | 7 | 0.28 | 21 | 2.24 | 0 | 100 | 90 |
| 0.07 | 7 | 0.28 | 21 | 2.24 | 0 | 100 | 95 |
| 0.56 | 7 | 0.28 | 15 | 2.24 | 5 | 100 | 98 |
| 0.28 | 7 | 0.28 | 15 | 2.24 | 0 | 100 | 95 |
| 0.14 | 7 | 0.28 | 15 | 2.24 | 0 | 100 | 95 |
| 0.07 | 7 | 0.28 | 15 | 2.24 | 0 | 100 | 85 |
| 0.56 | 7 | 0.28 | 17 | 2.24 | 15 | 99 | 98 |
| 0.28 | 7 | 0.28 | 17 | 2.24 | 5 | 100 | 98 |
| 0.14 | 7 | 0.28 | 17 | 2.24 | 0 | 100 | 95 |
| 0.07 | 7 | 0.28 | 17 | 2.24 | 0 | 100 | 85 |
| 0.56 | 12 | 0.28 | — | — | 45 | 99 | 90 |
| 0.28 | 12 | 0.28 | — | — | 30 | 99 | 95 |
| 0.14 | 12 | 0.28 | — | — | 10 | 99 | 90 |
| 0.07 | 12 | 0.28 | — | — | 5 | 99 | 85 |
| 0.56 | 12 | 0.28 | 18 | 2.24 | 15 | 99 | 95 |
| 0.28 | 12 | 0.28 | 18 | 2.24 | 10 | 100 | 95 |
| 0.14 | 12 | 0.28 | 18 | 2.24 | 0 | 99 | 99 |
| 0.07 | 12 | 0.28 | 18 | 2.24 | 0 | 100 | 80 |
| 0.56 | 12 | 0.28 | 19 | 2.24 | 20 | 99 | 99 |
| 0.28 | 12 | 0.28 | 19 | 2.24 | 5 | 100 | 95 |
| 0.14 | 12 | 0.28 | 19 | 2.24 | 0 | 99 | 85 |
| 0.07 | 12 | 0.28 | 19 | 2.24 | 0 | 99 | 85 |
| 0.56 | 12 | 0.28 | 20 | 2.24 | 10 | 100 | 98 |
| 0.28 | 12 | 0.28 | 20 | 2.24 | 5 | 100 | 98 |
| 0.14 | 12 | 0.28 | 20 | 2.24 | 5 | 100 | 95 |
| 0.07 | 12 | 0.28 | 20 | 2.24 | 0 | 99 | 90 |
| 0.56 | 12 | 0.28 | 21 | 2.24 | 20 | 99 | 98 |
| 0.28 | 12 | 0.28 | 21 | 2.24 | 10 | 100 | 98 |
| 0.14 | 12 | 0.28 | 21 | 2.24 | 5 | 99 | 95 |
| 0.07 | 12 | 0.28 | 21 | 2.24 | 0 | 100 | 90 |

TABLE 24-continued

| Herb. No. 1 | Co-Herb. | | Antidote | | % Inhibition | | |
|---|---|---|---|---|---|---|---|
| Kg/ha | No. | Kg/ha | No. | Kg/ha | Corn | GFT | VL |
| 0.56 | 12 | 0.28 | 15 | 2.24 | 5 | 99 | 99 |
| 0.28 | 12 | 0.28 | 15 | 2.24 | 5 | 100 | 98 |
| 0.14 | 12 | 0.28 | 15 | 2.24 | 5 | 99 | 95 |
| 0.07 | 12 | 0.28 | 15 | 2.24 | 5 | 99 | 90 |
| 0.56 | 12 | 0.28 | 17 | 2.24 | 20 | 100 | 95 |
| 0.28 | 12 | 0.28 | 17 | 2.24 | 5 | 98 | 98 |
| 0.14 | 12 | 0.28 | 17 | 2.24 | 5 | 199 | 98 |
| 0.07 | 12 | 0.28 | 17 | 2.24 | 5 | 99 | 90 |
| 0.56 | 6 | 0.14 | — | — | 40 | 100 | 95 |
| 0.28 | 6 | 0.14 | — | — | 25 | 100 | 95 |
| 0.14 | 6 | 0.14 | — | — | 20 | 100 | 95 |
| 0.07 | 6 | 0.14 | — | — | 5 | 100 | 85 |
| 0.56 | 6 | 0.14 | 18 | 2.24 | 20 | 100 | 98 |
| 0.28 | 6 | 0.14 | 18 | 2.24 | 5 | 99 | 95 |
| 0.14 | 6 | 0.14 | is | 2.24 | 0 | 99 | 95 |
| 0.07 | 6 | 0.14 | 18 | 2.24 | 0 | 100 | 90 |
| 0.56 | 6 | 0.14 | 19 | 2.24 | 10 | 99 | 99 |
| 0.28 | 6 | 0.14 | 19 | 2.24 | 5 | 99 | 95 |
| 0.14 | 6 | 0.14 | 19 | 2.24 | 0 | 100 | 95 |
| 0.07 | 6 | 0.14 | 19 | 2.24 | 0 | 100 | 90 |
| 0.56 | 6 | 0.14 | 20 | 2.24 | 20 | 100 | 95 |
| 0.28 | 6 | 0.14 | 20 | 2.24 | 5 | 100 | 98 |
| 0.14 | 6 | 0.14 | 20 | 2.24 | 5 | 99 | 90 |
| 0.07 | 6 | 0.14 | 20 | 2.24 | 0 | 100 | 95 |
| 0.56 | 6 | 0.14 | 21 | 2.24 | 10 | 100 | 98 |
| 0.28 | 6 | 0.14 | 21 | 2.24 | 5 | 99 | 95 |
| 0.14 | 6 | 0.14 | 21 | 2.24 | 5 | 100 | 90 |
| 0.07 | 6 | 0.14 | 21 | 2.24 | 0 | 100 | 85 |
| 0.56 | 6 | 0.14 | 15 | 2.24 | 10 | 99 | 99 |
| 0.28 | 6 | 0.14 | 15 | 2.24 | 10 | 100 | 98 |
| 0.14 | 6 | 0.14 | 15 | 2.24 | 5 | 100 | 85 |
| 0.07 | 6 | 0.14 | 15 | 2.24 | 5 | 100 | 95 |
| 0.56 | 6 | 0.14 | 17 | 2.24 | 15 | 99 | 98 |
| 0.28 | 6 | 0.14 | 17 | 2.24 | 15 | 98 | 95 |
| 0.14 | 6 | 0.14 | 17 | 2.24 | 0 | 100 | 90 |
| 0.07 | 6 | 0.14 | 17 | 2.24 | 5 | 100 | 90 |
| 0.56 | 4 | 1.12 | — | — | 40 | 75 | 90 |
| 0.28 | 4 | 1.12 | — | — | 25 | 85 | 95 |
| 0.14 | 4 | 1.12 | — | — | 20 | 80 | 90 |
| 0.07 | 4 | 1.12 | — | — | 10 | 70 | 90 |
| 0.56 | 4 | 1.12 | 18 | 2.24 | 10 | 65 | 90 |
| 0.28 | 4 | 1.12 | 18 | 2.24 | 5 | 70 | 95 |
| 0.14 | 4 | 1.12 | 18 | 2.24 | 5 | 55 | 95 |
| 0.07 | 4 | 1.12 | 18 | 2.24 | 5 | 65 | 90 |
| 0.56 | 4 | 1.12 | 19 | 2.24 | 5 | 70 | 90 |
| 0.28 | 4 | 1.12 | 19 | 2.24 | 5 | 45 | 95 |
| 0.14 | 4 | 1.12 | 19 | 2.24 | 0 | 60 | 95 |
| 0.07 | 4 | 1.12 | 19 | 2.24 | 0 | 40 | 90 |
| 0.56 | 4 | 1.12 | 20 | 2.24 | 10 | 65 | 95 |
| 0.28 | 4 | 1.12 | 20 | 2.24 | 0 | 65 | 90 |
| 0.14 | 4 | 1.12 | 20 | 2.24 | 0 | 40 | 90 |
| 0.07 | 4 | 1.12 | 20 | 2.24 | 0 | 65 | 90 |
| 0.56 | 4 | 1.12 | 21 | 2.24 | 5 | 70 | 90 |
| 0.28 | 4 | 1.12 | 21 | 2.24 | 0 | 65 | 95 |
| 0.14 | 4 | 1.12 | 21 | 2.24 | 5 | 60 | 90 |
| 0.07 | 4 | 1.12 | 21 | 2.24 | 5 | 65 | 90 |
| 0.56 | 4 | 1.12 | 15 | 2.24 | 15 | 60 | 95 |
| 0.28 | 4 | 1.12 | 15 | 2.24 | 5 | 60 | 95 |
| 0.14 | 4 | 1.12 | 15 | 2.24 | 10 | 65 | 95 |
| 0.07 | 4 | 1.12 | 15 | 2.24 | 0 | 40 | 90 |
| 0.56 | 4 | 1.12 | 17 | 2.24 | 20 | 70 | 95 |
| 0.28 | 4 | 1.12 | 17 | 2.24 | 5 | 45 | 90 |
| 0.14 | 4 | 1.12 | 17 | 2.24 | 0 | 50 | 90 |
| 0.07 | 4 | 1.12 | 17 | 2.24 | 0 | 55 | 90 |

The data in Table 24 show that in all cases, combinations of Herbicide No. 1 at test rates of 0.28 kg/ha and 0.56 kg/ha and each Co-herbicide at rates between 0.14 kg/ha and 1.12 kg/ha, resulted in commercially-unacceptable injury to the corn crop. Moreover, combinations of Herbicide No. 1 at rates as low as 0.14 kg/ha and rates of 0.14 kg/ha for Co-herbicide No. 6 and 1.12 kg/ha for Co-herbicide No. 4, also resulted in commercially-unacceptable injury to corn.

In contrast, the addition of each of the test antidotes at an application rate of 2.24 kg/ha to combinations of Herbicide No. 1 at rates of less than 0.56 kg/ha and the indicated rate of co-herbicide, uniformally reduced corn injury to commercially-acceptable levels. In fact, only Antidote No.s 17, 18, 19 and 20 failed to safen said herbicide:co-herbicide combinations at the highest test rate (0.56 kg/ha) of Herbicide No. 1.

In addition, control of the weed species was generally unaffected by addition of an antidote, particularly with regard to Velvetleaf. There was a noticeable reduction in control of Giant foxtail at some test rates of less than 0.56 kg/ha of Herbicide No. 1 and Co-herbicide No. 4 at 1.12 kg/ha, when Antidote Nos. 15 and 17–21 were present.

EXAMPLE 25

Additional tests were conducted in the greenhouse in order to evaluate the antidotal efficacy of Antidote Nos. 1 (dichlormid) and 2 (naphthalic anhydride) in protecting corn from the herbicidal activity of Herbicide Nos. 1–3 (i.e., NC-319, NC-319 EX and NC-311, respectively). The chemicals were tested in both preemergence and postemergence modes of application. The herbicides were prepared and applied as wettable powders; dichlormid was applied as an emulsifiable concentrate, while the naphthalic anhydride was applied as a coating on the corn seed prior to planting.

Corn seeds (Pioneer 3424 variety) were planted in alluvial soil containing compost and fertilizer in pots 12 cm. in diameter. Test chemicals were applied with a spray gun at the spray volume rate of 11.2 l/ha at the time of seeding in the preemergence tests and seven (7) days after seeding in the post-emergence tests, when the check (control) plants were at the 16–20 cm., 3.0–3.2 leaf stage, and naphthalic anhydride coated seed grown plants were at the 14–16 cm., 2.8–3.0 leaf stage.

Test data from the preemergence tests are shown in Table 25A and from the post-emergence tests in Table 25B. In the tables, the concentration of chemicals is shown in terms of active ingredient in grams per hectare (G/ha); concentrations of the naphthalic anhydride were not measured per se, but were present as in conventional, normally-coated applications. Corn injury is shown in terms of percent inhibition of growth.

TABLE 25A

| Preemergence | | | | |
|---|---|---|---|---|
| Herbicide | | Antidote | | % Inhibition |
| No. | G/ha | No. | G/ha | Corn |
| 1 | 0.25 | — | — | 22.3 |
| 1 | 0.74 | — | — | 32.3 |
| 1 | 2.5 | — | — | 49.9 |
| 2 | 0.25 | — | — | 21.7 |
| 2 | 0.74 | — | — | 36.4 |
| 2 | 2.5 | — | — | 42.7 |
| 3 | 0.07 | — | — | 19.1 |
| 3 | 0.25 | — | — | 80.9 |
| 3 | 0.74 | — | — | 80.9 |
| — | — | 2 | * | 17.4 |
| 1 | 0.25 | 2 | " | 18.2 |
| 1 | 0.74 | 2 | " | 31.2 |
| 1 | 2.5 | 2 | " | 27.3 |
| 2 | 0.25 | 2 | " | 31.5 |
| 2 | 0.74 | 2 | " | 18.9 |
| 2 | 2.5 | 2 | " | 31.9 |
| 3 | 0.07 | 2 | " | 13.2 |
| 3 | 0.25 | 2 | " | 29.3 |
| 3 | 0.74 | 2 | " | 46.9 |

TABLE 25A-continued

| Preemergence | | | | |
|---|---|---|---|---|
| Herbicide | | Antidote | | % Inhibition |
| No. | G/ha | No. | G/ha | Corn |
| — | — | 1 | 7.41 | 21.0 |
| 1 | 0.25 | 1 | 7.41 | 23.2 |
| 1 | 0.74 | 1 | 7.41 | 28.4 |
| 1 | 2.5 | 1 | 7.41 | 26.2 |
| 2 | 0.25 | 1 | 7.41 | 26.5 |
| 2 | 0.74 | 1 | 7.41 | 28.9 |
| 2 | 2.5 | 1 | 7.41 | 37.3 |
| 3 | 0.07 | 1 | 7.41 | 9.3 |
| 3 | 0.25 | 1 | 7.41 | 43.0 |
| 3 | 0.74 | 1 | 7.41 | 83.9 |

*Seed treatment antidote concentration not measured.

TABLE 25B

| Post-emergence | | | | |
|---|---|---|---|---|
| Herbicide | | Antidote | | % Inhibition |
| No. | G/ha | No. | G/ha | Corn |
| 1 | 0.25 | — | — | 12.4 |
| 1 | 0.74 | — | — | 9.2 |
| 1 | 2.5 | — | — | 24.5 |
| 2 | 0.25 | — | — | 23.7 |
| 2 | 0.74 | — | — | 14.9 |
| 2 | 2.5 | — | — | 17.6 |
| 3 | 0.07 | — | — | 42.2 |
| 3 | 0.25 | — | — | 76.5 |
| 3 | 0.74 | — | — | 76.1 |
| — | — | 2 | * | 14.5 |
| 1 | 0.25 | 2 | " | 14.1 |
| 1 | 0.74 | 2 | " | 27.3 |
| 1 | 2.5 | 2 | " | 16.7 |
| 2 | 0.25 | 2 | " | 8.0 |
| 2 | 0.74 | 2 | " | 24.9 |
| 2 | 2.5 | 2 | " | 19.0 |
| 3 | 0.07 | 2 | " | 20.4 |
| 3 | 0.25 | 2 | " | 33.7 |
| 3 | 0.74 | 2 | " | 58.8 |
| — | — | 1 | — | 1.4 |
| 1 | 0.25 | 1 | 7.41 | 16.1 |
| 1 | 0.74 | 1 | 7.41 | 16.3 |
| 1 | 2.5 | 1 | 7.41 | 22.4 |
| 2 | 0.25 | 1 | 7.41 | 17.6 |
| 2 | 0.74 | 1 | 7.41 | 15.9 |
| 2 | 2.5 | 1 | 7.41 | 23.7 |
| 3 | 0.07 | 1 | 7.41 | 39.8 |
| 3 | 0.25 | 1 | 7.41 | 73.9 |
| 3 | 0.74 | 1 | 7.41 | 73.1 |

*Seed treatment antidote concentration not measured.

Referring to the preemergence data in Table 25A, it is shown that the addition of Antidote 2 significantly reduced corn injury due to each of Herbicide Nos. 1–3 at the two highest rates of herbicide application. A similar pattern of safening of those herbicides was accomplished when Antidote No. 1 was applied at 7.41 G/ha, especially at the highest rate of herbicide application, with the notable exception of Herbicide No. 3 at 0.74 G/ha where a slight increase in corn injury was noted, although at the 0.25 G/ha rate Herbicide No. 3 was markedly safened by Antidote No. 1, i.e., from 80.9% inhibition to 43.0% inhibition.

In the post-emergence tests, the data in Table 25B showed that Antidote No. 2 significantly reduced corn injury by Herbicides No. 1 and 3 at the highest rates of application, but not at lower rates. In these tests, Antidote No. 1 did not exhibit noticeable safening effect when applied post-emergence to Herbicide Nos. 1–3.

EXAMPLE 26

In order to better understand and to confirm the results of greenhouse tests with herbicidal compositions comprising representative compounds according to Formula I and an antidote with and without a co-herbicide, a large number of field trials were conducted. This example provides a summary of those field trials.

The primary purpose of the field trials summarized herein was to ascertain the amount of corn injury caused by a compound according to Formula I. viz. Herbicide No. 1, with and without a co-herbicide of the α-chloroacetanilide class, viz., Herbicide Nos. 6 and 7, and the extent that any corn injury could be safened by a dichloroacetamide antidotal compound, viz., Antidote No. 15.

Corn injury is generally expressed, in broad terms, in stand reduction, growth reduction, malformed plants and other more specific effects. For purposes of the summary here, the results of a plurality of field trials are expressed in terms of growth reduction (GR), i.e., a significant reduction in plant height of the corn stand. A common criteria for commercially-acceptable corn injury is an amount equal to or less than 10% malformed plants or stand reduction and for present reporting purposes, no greater than about 15% growth reduction. The corn injury/safening described for these field trials refers to commercially-unacceptable to commercially-acceptable performance.

In the field trials from a wide distribution of trial locations, soil types (all having in excess of 2% organic matter), climatic effects, etc., the test chemicals were applied as tank mixes in various modes of application, i.e., pre-plant incorporation (PPI) and preemergence surface application (PRE). Test plots were small plots with three replications in a randomized complete block design. Observations were made and recorded in a period of from 31–50 days after treatment.

In summary, in PPI trials, Herbicide No. 1 applied at an active ingredient rate of 0.07 and 0.14 kg/ha in combination with Herbicide No. 7 (alachlor) as co-herbicide and without an antidote resulted in 9.75% and 13.25% GR, respectively. However, with the addition of Antidote No. 15 at a ratio of 1:1 of Antidote No. 15 to Herbicide No. 1, corn injury was reduced to 7.75% and 9.82%, respectively. More importantly, maximum injury levels were reduced from 48% (due to Herbicide No. 1 at the 0.07 and 0.14 kg/ha application rates) to 22 and 26% GR.

When Herbicide No. 6 (acetochlor) was combined with Herbicide No. 1 at active ingredient rates of 0.7, 0.14 and 0.28 kg/ha, corn injury levels without an antidote were, respectively, 12.5%, 14.9% and 24.9% GR. Addition of Antidote No. 15 to this composition reduced said corn injury levels to, respectively, 8.6%, 10.3% and 12.5% GR. Again importantly, at the above rates of chemicals, the frequency of corn injury exceeding 20% GR was reduced, respectively, from 5 injured plants out of 27 to 1 of 27; from 7 of 27 to 1 of 27 and from 15 of 27 to 2 of 27.

In the preemergent surface application of chemicals trials, combinations of Herbicides No. 1 and acetochlor at active ingredient rates of 0.07, 0.14 and 0.28 kg/ha, resulted in 9.8%, 13.4% and 20.3% GR, respectively. Addition of Antidote No. 15 to that composition reduced growth reduction injury to 8.7%, 8.2% and 14.5%, respectively. Increased ratios of Antidote No. 15 to Herbicide No. 1 to 3:1 reduced crop injury even further.

Results of the above field trials showed that under most conditions Antidote No. 15 effectively reduced corn GR injury induced by Herbicide No. 1, representative of the pyrazolylsulfonylurea herbicides of Formula I, to commercially-acceptable levels.

As will be apparent, the data in the above tables reflect the fact that the safening effect on various herbicides by various safeners will have different degrees of effect depending upon a variety of factors, including, relative concentrations of herbicides and/or co-herbicides and/or antidotes, weather and soil conditions, water content, etc., as well appreciated in the art.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1–60%, preferably 5–50% by weight of active ingredient, the upper limit being determined by the solubility limit of active ingredient in the solvent. Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 5 to 94 parts solvent, all parts being be weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, imidazolinones, sulfonylureas, carbamates, acetamides, acetanilides, uracils, acetic acid or phenol derivatives, thiolcarbamates, triazoles, benzoic acid and its derivatives, nitriles, biphenyl ethers, nitrobenzenes, etc.

Fertilizers useful in combination with the active ingredients include, for example, ammonium nitrate, urea, potash and superphosphate. Other useful additaments include materials in which plant organisms take root and grow such as compost, manure, humus, sand and the like.

As will be appreciated by those skilled in the art, the practice of this invention comprises the use of the antidotal compounds disclosed and claimed herein with any herbicidally-active pyrazolylsulfonylurea or derivative compound which may optionally be combined with co-herbicides from many different classes of chemistry. Obviously, the above listings of exemplary compounds is not intended to be exhaustive, but representative. Again, as noted earlier herein, it is expected that not every combination of herbicide and antidote will result in safening of all crops, but it is within the skill of the art to test any given herbicide/antidote combination in plant screens of any spectrum of plants and note the results.

The foregoing embodiments illustrate that the combinations of herbicide and antidote of this invention are useful in controlling weeds while reducing herbicidal injury to crop plants under greenhouse and field test conditions.

The herbicide, antidote, or a mixture thereof, may be applied to the plant locus without any adjuvants other than a solvent. As indicated above, these mixtures may be in the form of emulsifiable concentrates, microencapsulates, particulate solids, granules of varying particle size, e.g., water-dispersible or water-soluble granules or larger dry granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention may contain from about 5 to 95 parts herbicide and antidote, about 1 to 50 parts surface-active agent, and about 4 to 94 parts solvent, all parts being by weight based on the total weight of the composition.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed coating and for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzene-sulfonate and the sodium salts of alkylnaphthalene-sulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols and mercaptans.

The invention herein has been specifically exemplified with a preferred member of the class of pyrazolylsulfonylurea herbicidal compounds identified above in Formulae I and IA and several commercial herbicides, as representative of the co-herbicidal component together with a plurality of antidotal compounds as representative of the compounds according to Formulae II and III. It is to be understood that other compounds within the scope of the above formulae and other chemical classes are specifically contemplated as within the scope of this invention either as the herbicidal component or as a co-herbicide.

The above specifically mentioned antidotal compounds and herbicidal compounds used alone and/or as co-herbicides herein are intended merely as exemplary of the classes of compounds which they represent. However, it is expressly contemplated that many other herbicidal and antidotal compounds analogous to those represented herein having a variety of equivalent radicals substituted on the central nuclei may similarly be used in compositions to safen various crop plants to a greater or lesser extent similarly as exemplified hereinabove. For example, other α-haloacetamide and α-haloacetanilide compounds useful as co-herbicides herein are described in U.S. Pat. Nos. 3,442,945, 3,547,620, 3,574,746, 3,586,496, 3,830,841, 3,901,768, 4,249,935, 4,319,918, 4,517,011, 4,601,745, 4,657,579 and 4,666,502 and Australian Patent No. AU-A1-18044/88.

Herbicidally-useful thiocarbamate compounds are described in U.S. Pat. Nos. 2,913,327, 3,330,643 and 3,330,821.

Other herbicidal pyridine compounds are described in U.S. Pat. Nos. 4,692,184, 4,826,532 and 4,988,384.

Herbicidally-useful heterocycyl phenyl ethers (especially pyrazolyl aryl ethers) are described, e.g., in U.S. Pat. No. 4,298,749.

Herbicidal diphenyl ethers and nitrophenyl ethers include 2,4-dichlorophenyl 4'-nitrophenyl ether ("nitrofen"), 2-chloro-1-(3'-ethoxy-4'-nitrophenoxy)-4-trifluoromethylbenzene ("Oxyfluorfen"), 2', 4'-dichlorophenyl 3-methoxy-4-nitrophenyl ether ("Chlormethoxynil"), methyl 2-[4'-(2', 4'-dichlorophenoxy)-phenoxy]propionate, N-(2'-phenoxyethyl)-2-[5'-(2"-chloro-4"-trifluoromethylphenoxy)-phenoxy]-propionamide, 2-methoxyethyl 2-[nitro-5-(2-chloro-4-trifluoromethylphenoxy)-phenoxypropionate and 2-chloro-4-trifluoromethylphenyl 3'-oxazolin-2'-yl-4'-nitrophenylether.

Another generic class of agrichemically-important herbicidal compounds specifically contemplated for use as co-herbicidal compounds in combination with the antidotal compounds of this invention are the urea derivatives. Important herbicidal ureas include 1-(benzothiazol-2-yl)-1,3-dimethylurea; phenylureas, for example: 3-(3-chloro-p-tolyl)-1, 1-dimethylurea ("chlorotoluron"), 1,1-dimethyl-3-(α,α,α-trifluoro-m-tolyl) urea ("fluometuron"), 3-(4-bromo-3-chlorophenyl) -methoxy-1-methylurea ("chlorbromuron"), 3-(4-bromophenyl) -1-methoxy-1-methylurea ("metobromuron") , 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron") and 3-(3-chloro-4-methoxyphenyl)-1,1-dimethylurea ("metoxuron");

Important herbicidal sulfonylureas and sulfonamides specifically contemplated as useful as the herbicidal component herein in compositions with the antidotal compounds of this invention include those disclosed in the following patents: U.S. Pat. Nos. 4,383,113, 4,127,405, 4,343,649, 4,479,821, 4,481,029, 4,514,212, 4,420,325, 4,638,004, 4,675,046, 4,681,620, 4,741,760, 4,723,123, 4,411,690, 4,718,937, 4,620,868, 4,668,277, 4,592,776, 4,666,508, 4,696,695, 4,731,446, 4,678,498, 4,786,314, 4,889,550, 4,931,081 and 4,668,279; EP Published Application Numbers 084224, 173312, 147365, 87780, 190105, 256396, 264021, 264672, 142152, 244847, 176304, 177163, 187470, 187489, 184385, 232067, 234352, 189069, 224842, 249938, 246984 and 282613, and German Offen. DE 3,618,004.

Other herbicidal imidazolinone or imidazolidinone or -dione compounds useful as the co-herbicidal component in compositions within the purview of this invention which may be safened for use in various crops include the compounds disclosed in following exemplary publications: EP Numbers 041623, 133310, 198552, 216360 and 298029; JA 1109-790, JA 1197-580A, J6 1183-272A and J6 3196-750A; and Australian published Application No. AU 8661-073A, GB 2 172 886A and U.S. Pat. Nos. 4,188,487, 4,297,128, 4,562,257, 4,554,013, 4,647,301, 4,638,068, 4,650,514, 4,709,036, 4,749,403, 4,749,404, 4,776,619, 4,798,619 and 4,741,767.

Still other classes of herbicidal compounds contemplated for combination with the herbicidal and antidotal components of this invention include the following representative species:

Triazines and triazinones: 2,4-bis-(isopropylamino)-6-methylthio-1,3,5-triazine ("prometryn"), 2,4-bis-(ethylamino)-6-methylthio-1,3,5-triazine ("simetryn"), 2-(1',2'-dimethylpropylamino)-4-ethylamino-6-methylthio-1,3,5-triazine ("dimethametryn"), 2-(chloro-4,6-bis(ethylamino)-1,3,5-triazine ("simazine"), 2-tert-butylamino- 4-chloro-6-ethylamino-1,3,5-triazine ("terbuthylazine"), 2-tert-butylamino-4-ethylamino-6-methoxy-1,3,5-triazine ("terbumeton"), 2-tertbutylamino-4-ethylamino-6-methylthio-1,3,5-triazine ("terbutryn"), 2-ethylamino-4-isopropylamino-6-methylthio-1,3,5-triazine ("ametryn") and 3,4-bis-(methylamino)-6-tert-butyl-4,4-dihydro-1,2,-4-triazin-5-one.

Oxadiazolones: 5-tert-butyl-3-(2', 4'-dichloro-5'-isopropoxyphenyl)-1,3,4-oxadiazol-2-one ("Oxadiazon").

Phosphates: S-2-methylpiperidinocarbonylmethyl O,O-dipropyl phosphorodithioate ("Piperophos").

Pyrazoles: 1,3-dimethyl-4-(2',4'-dichlorobenzolyl)-5-(4'-tolylsulfonyloxy)-pyrazole; aryl- and heterocyclic-substituted pyrazoles, e.g., as exemplified in EP No. 0361114; Japanese Kokai No. JP 50137061 and U.S. Pat. No. 4,008,249. Preferred species of such substituted-pyrazole compounds include 4-chloro-3-(4-chloro-2-fluoro-5-(2-propynyloxy)phenyl)-1-methyl- 5-(methylsulfonyl)-1H pyrazole and analogs thereof, e.g., where the substituent in the 5-position of the pyrazole ring is a haloalkyl radical, preferably $CF_3$.

Also α-(phenoxyphenoxy)-propionic acid derivatives and α-pyridyl-2-oxyphenoxy)-propionic acid derivatives.

Other herbicidal compounds useful as co-herbicides herein include aromatic and heterocyclic di- and triketones exemplified in U.S. Pat. Nos. 4,797,147, 4,853,028, 4,854, 966, 4,855,477, 4,938,796 and 4,869,748.

Still other co-herbicidal compounds contemplated herein are pyrrolidinones, e.g, the 1-phenyl-3-carboxyamidopyrrolidinones disclosed in U.S. Pat. No. 4,874,422, and the 1-phenyl-4-haloalkylpyrrolidones disclosed in U.S. Pat. No. 4,515,627, etc.

Still other herbicidal compounds useful as co-herbicides herein include benzoic acid derivatives of the type exemplified by 5-(2'-chloro-4'-trifluoromethylphenoxy)-2-nitrobenzoic acid ("Acifluorfen"), 2,6-dichlorobenzonitrile ("dichlobenil"), 3,6-dichloro-2-methoxybenzoic acid ("dicamba"), etc. and compounds disclosed in U.S. Pat. Nos. 3,013,054, 3,027,248 and 3,979,437, etc.

In addition to the antidotal compounds exemplified herein, other representative antidotal compounds according to Formula II and III or other structure are expressly disclosed in various patents, e.g., U.S. Pat. Nos. 3,959,304, 4,072,688, 4,137,070, 4,124,372, 4,124,376, 4,483,706, 4,636,244, 4,033,756, 4,493,726, 4,708,735, 4,256,481, 4,199,506, 4,251,261, 4,070,389, 4,231,783, 4,269,775, 4,152,137, 4,755,218, 4,964,893, 4,623,727, 4,822,884, 4,851,031, 4,902,340, 4,749,406, 4,758,264, 4,785,105, 4,785,106, 4,900,350 and 4,294,764, and EP Nos. 159,287, 159,290, 258,184, 94,349, 2,121,403, 0253291, 0007588, 0190105, 0229649, and 16618 and W. German Patent Application Nos. 28 28 222, 28 28 293.1, and 29 30 450.5, South African Patent No. 82/7681 and PRC Application No. 102 879-87.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

I claim:

1. Composition comprising a herbicidally-effective amount of NC-319 and an antidotally-effective amount of oxazolidine, 3-(dichloroacetyl)-2,2-dimethyl-5-(2-furanyl).

2. Composition comprising
   (a) a herbicidally-effective amount of NC-319;
   (b) an antidotally-effective amount of oxazolidine, 3-(dichloroacetyl)-2,2-dimethyl-5-(2-furanyl)- and
   (c) a co-herbicidal compound selected from the group consisting of acetochlor, alachlor, butachlor, metolachlor, pretilachlor, dimethachlor and metazachlor.

3. Composition according to claim 2 wherein said co-herbicidal compound is acetochlor.

4. Composition according to claim 2 wherein said co-herbicidal compound is alachlor.

5. Method for reducing phytotoxicity to corn plants due to the pre-emergent application of NC-319, which comprises applying to the locus of said corn plants prior to the emergence thereof an antidotally effective amount of oxazolidine, 3-(dichloroacetyl)-2,2-dimethyl-5-(2-furanyl).

6. Method for reducing phytotoxicity to corn plants due to the pre-emergent application of NC-319 which comprises applying to the locus of said corn plants prior to emergence thereof an antidotally effective amount of oxazolidine, 3-(dichloroacetyl)-2,2-dimethyl-5-(2-furanyl)- and a co-herbicidal compound selected from the group consisting of acetochlor, alachlor, butachlor, metolachlor, pretilachlor, dimethachlor and metazachlor.

7. Method according to claim 6 wherein said co-herbicidal compound is acetochlor.

8. Method according to claim 6 wherein said co-herbicidal compound is alachlor.

* * * * *